(12) United States Patent
Gatayama et al.

(10) Patent No.: US 11,317,886 B2
(45) Date of Patent: May 3, 2022

(54) X-RAY CT APPARATUS AND IMAGING MANAGEMENT APPARATUS

(71) Applicant: CANON MEDICAL SYSTEMS CORPORATION, Otawara (JP)

(72) Inventors: Kazuki Gatayama, Otawara (JP); Shinsuke Tsukagoshi, Nasushiobara (JP); Katsuhiko Ishida, Nasushiobara (JP); Kusuto Koga, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 23 days.

(21) Appl. No.: 15/879,966

(22) Filed: Jan. 25, 2018

(65) Prior Publication Data
US 2018/0206811 A1 Jul. 26, 2018

(30) Foreign Application Priority Data

Jan. 25, 2017 (JP) .............................. JP2017-011075
Jan. 24, 2018 (JP) .............................. JP2018-009390

(51) Int. Cl.
*A61B 6/03* (2006.01)
*A61B 6/00* (2006.01)
(Continued)

(52) U.S. Cl.
CPC .............. *A61B 6/545* (2013.01); *A61B 6/032* (2013.01); *A61B 6/465* (2013.01); *A61B 6/5235* (2013.01);
(Continued)

(58) Field of Classification Search
CPC ... A61B 6/4233; A61B 6/4241; A61B 6/4266; A61B 6/4275
See application file for complete search history.

(56) References Cited

U.S. PATENT DOCUMENTS

2003/0108149 A1 6/2003 Tsuyuki
2004/0114706 A1 6/2004 Ikeda et al.
(Continued)

FOREIGN PATENT DOCUMENTS

JP S59-017332 A 1/1984
JP 3-114445 5/1991
(Continued)

OTHER PUBLICATIONS

Japanese Office Action dated Nov. 9, 2021 in Japanese Patent Application No. 2018-009390, 4 pages.

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

An X-ray CT apparatus according to the embodiment executes an imaging according to an imaging protocol including one or more image elements corresponding to an imaging type. The X-ray CT apparatus includes an X-ray source, an X-ray detector and processing circuitry. The X-ray source radiates an X-ray. The X-ray detector detects the X-ray. The processing circuitry merges, when first and second imaging protocols are set, first and second imaging elements, respectively included in the first and second imaging protocols, corresponding to same imaging type into a single third imaging element, thereby generating a third imaging protocol including the third imaging element.

19 Claims, 15 Drawing Sheets

(51) Int. Cl.
*G01N 23/046* (2018.01)
*G06T 7/00* (2017.01)
*A61B 6/02* (2006.01)
*A61B 6/08* (2006.01)

(52) U.S. Cl.
CPC ......... *A61B 6/5241* (2013.01); *G01N 23/046* (2013.01); *G06T 7/0012* (2013.01); *A61B 6/027* (2013.01); *A61B 6/08* (2013.01); *A61B 6/4035* (2013.01); *A61B 6/481* (2013.01); *A61B 6/482* (2013.01); *A61B 6/488* (2013.01); *A61B 6/56* (2013.01); *G01N 2223/401* (2013.01); *G01N 2223/419* (2013.01); *G06T 2207/10124* (2013.01)

(56) References Cited

U.S. PATENT DOCUMENTS

| | | | |
|---|---|---|---|
| 2005/0201603 A1* | 9/2005 | Hristov | G06T 7/38 382/131 |
| 2007/0238963 A1* | 10/2007 | Kaminaga | A61B 6/488 600/407 |
| 2008/0234571 A1* | 9/2008 | Hay | A61B 6/542 600/425 |
| 2010/0232669 A1* | 9/2010 | Ziegler | G01T 1/2985 382/132 |
| 2011/0286574 A1* | 11/2011 | Suzuki | A61B 6/032 378/8 |
| 2012/0155605 A1 | 6/2012 | Yazaki | |
| 2012/0163687 A1 | 6/2012 | Plakas et al. | |
| 2013/0216019 A1* | 8/2013 | Maeda | A61B 6/484 378/19 |
| 2013/0259342 A1* | 10/2013 | Bruder | G06T 11/003 382/131 |
| 2013/0266117 A1* | 10/2013 | Ooshima | A61B 6/54 378/20 |
| 2014/0253544 A1* | 9/2014 | Arakita | A61B 6/032 345/419 |
| 2015/0297157 A1 | 10/2015 | Mukumoto | |
| 2016/0180525 A1* | 6/2016 | Reynolds | G06T 7/0016 382/131 |
| 2017/0296625 A1* | 10/2017 | Gardner | A61L 15/44 |
| 2017/0340299 A1* | 11/2017 | Grass | A61B 6/03 |
| 2018/0020993 A1 | 1/2018 | Tsukagoshi et al. | |
| 2018/0070908 A1* | 3/2018 | Netabayashi | A61B 6/542 |
| 2018/0235563 A1* | 8/2018 | Nam | A61B 5/742 |

FOREIGN PATENT DOCUMENTS

| | | |
|---|---|---|
| JP | 2001-286459 | 10/2001 |
| JP | 2003-245275 A | 9/2003 |
| JP | 2004-113779 A | 4/2004 |
| JP | 2006-55635 A | 3/2006 |
| JP | 2007-185358 A | 7/2007 |
| JP | 2008-012171 A | 1/2008 |
| JP | 2009-502403 A | 1/2009 |
| JP | 2009-285147 | 12/2009 |
| JP | 2012-130376 | 7/2012 |
| JP | 2012-130667 A | 7/2012 |
| JP | 2013-000479 A | 1/2013 |
| JP | 2014-054392 A | 3/2014 |
| JP | 2015-213749 A | 12/2015 |
| JP | 2018-020112 A | 2/2018 |

* cited by examiner

| LIST OF ORIGINAL PROTOCOL | |
|---|---|
| ORIGINAL PROTOCOL | EXECUTION ORDER |
| P1 | P11 S1 · P12 S2 · P13 S3 · P14 S2 · P15 S4 |
| P2 | P21 S1 · P22 S2 · P23 S2 |
| P3 | P31 S1 · P32 S3 · P33 S4 |

ORIGINAL PROTOCOL TO BE USED

P1: P11 S1 · P12 S2 · P13 S3 · P14 S2 · P15 S4

P2: P21 S1 · P22 S2 · P23 S2

SET

FIG. 4 ical Patent Application No. 2017-011075, filed on Jan. 25, 2017, and Japanese Patent Application No. 2018-009390, filed on Jan. 24, 2018, the entire contents of each of which are incorporated herein by reference.

X-RAY CT APPARATUS AND IMAGING MANAGEMENT APPARATUS

CROSS-REFERENCE TO RELATED APPLICATION

This application is based upon and claims the benefit of priority from Japanese Patent Application No. 2017-011075, filed on Jan. 25, 2017, and Japanese Patent Application No. 2018-009390, filed on Jan. 24, 2018, the entire contents of each of which are incorporated herein by reference.

FIELD

An embodiment as an aspect of the present invention relates to an X-ray computed tomography (CT) apparatus and an imaging management apparatus.

BACKGROUND

X-ray CT apparatus, which provides data on an object by means of images based on the intensity of X-rays transmitted through the object, have been playing an important role in various medical practices, including diagnostics and treatments of diseases, and surgical planning.

In the X-ray CT apparatus, various kinds of original imaging protocols (hereinafter simply referred to as "original protocol(s)") are preliminarily registered. Each original protocol includes data on original imaging elements (hereinafter referred to as "original element(s)") corresponding to one or more imaging types and includes an execution order of the original elements. In the X-ray CT apparatus, when a first original protocol is set to be used, an imaging condition is set for each original element in the first original protocol. Then, the first original protocol is executed according to the execution order of the multiple original elements. Next, in the X-ray CT apparatus, when a second original protocol is set to be used, an imaging condition is set for each original element in the second original protocol. Then, the second original protocol is executed according to the execution order of the original elements.

When the first and second original protocols are set to be used, it is conceivable that the first and second original protocols are preliminarily registered as one original protocol.

However, if original protocols are executed sequentially as planned to be used, there are cases where the executed original protocols include original elements having same imaging type. In that case, when there is overlapping of imaging areas in the original elements, X-ray exposure occurs redundantly on the overlapping portion.

BRIEF DESCRIPTION OF THE DRAWINGS

In accompanying drawings,

FIG. 4 is a diagram showing an example of a setting screen of the original protocol to be used, in the X-ray CT apparatus according to the embodiment;

Figure 3:
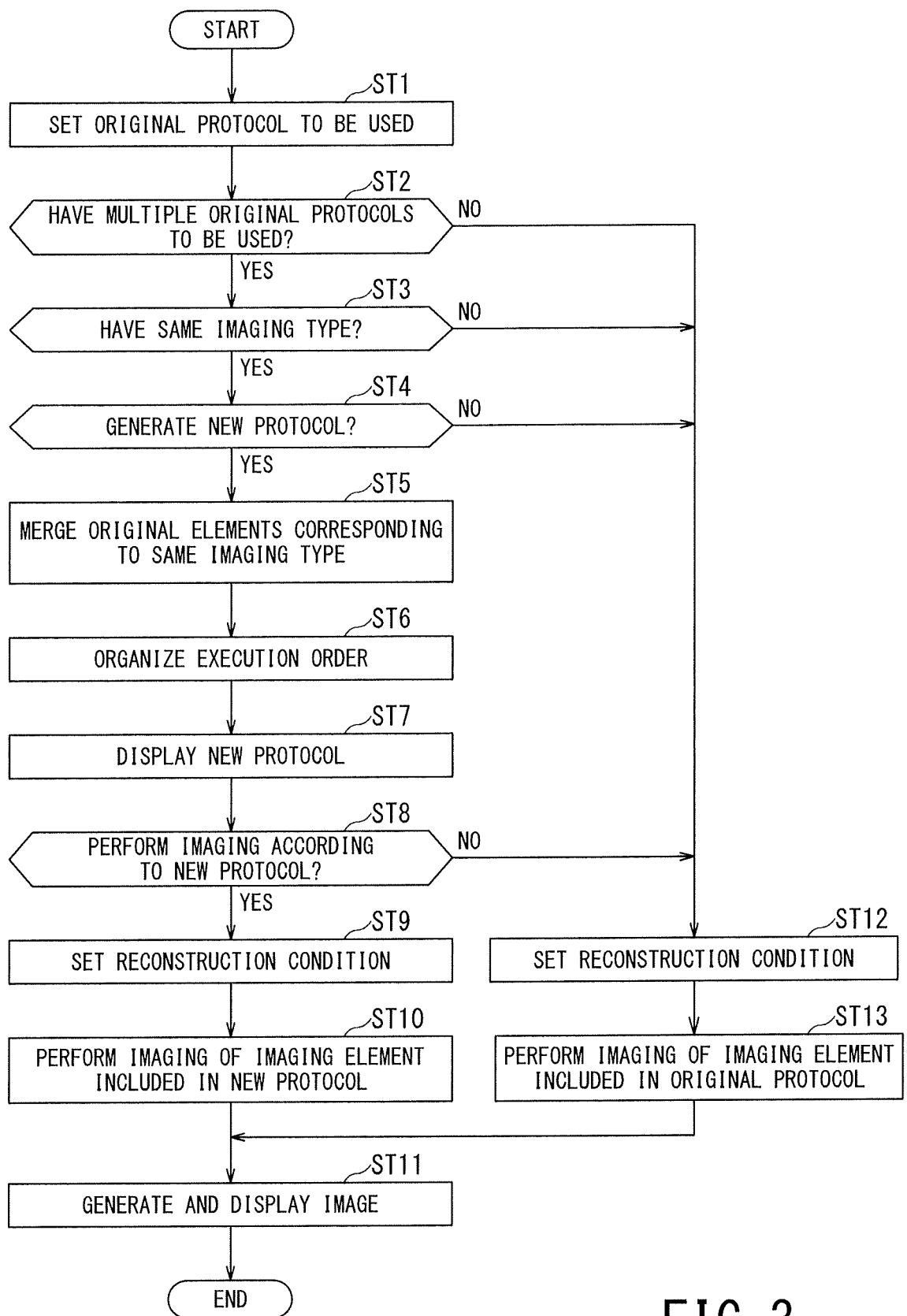
FIG. 3 is a flowchart showing an operation example of the X-ray CT apparatus according to the embodiment.
Figure 7:
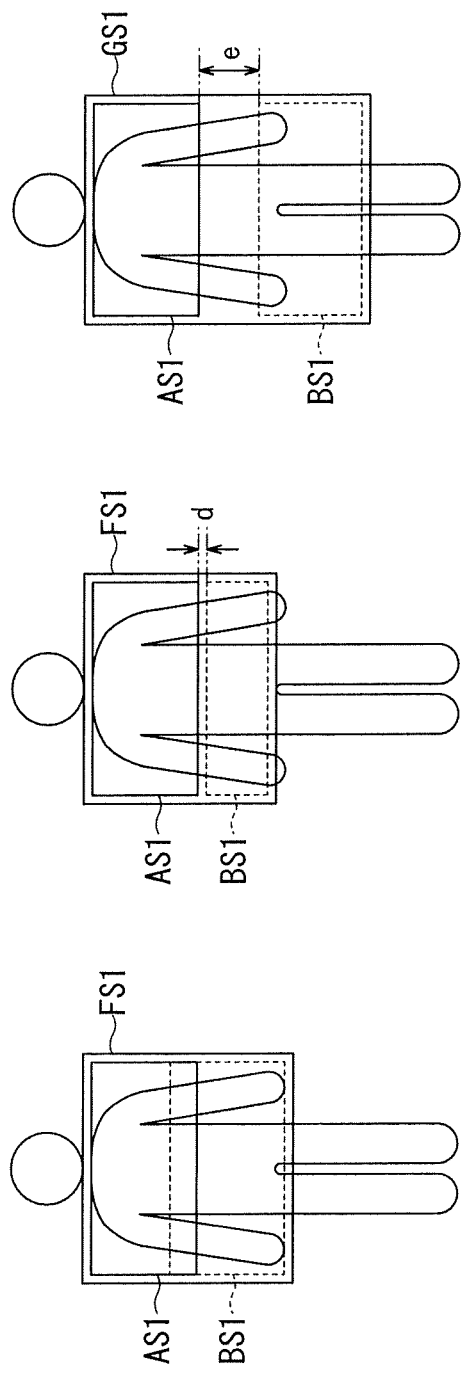
Figure 8:
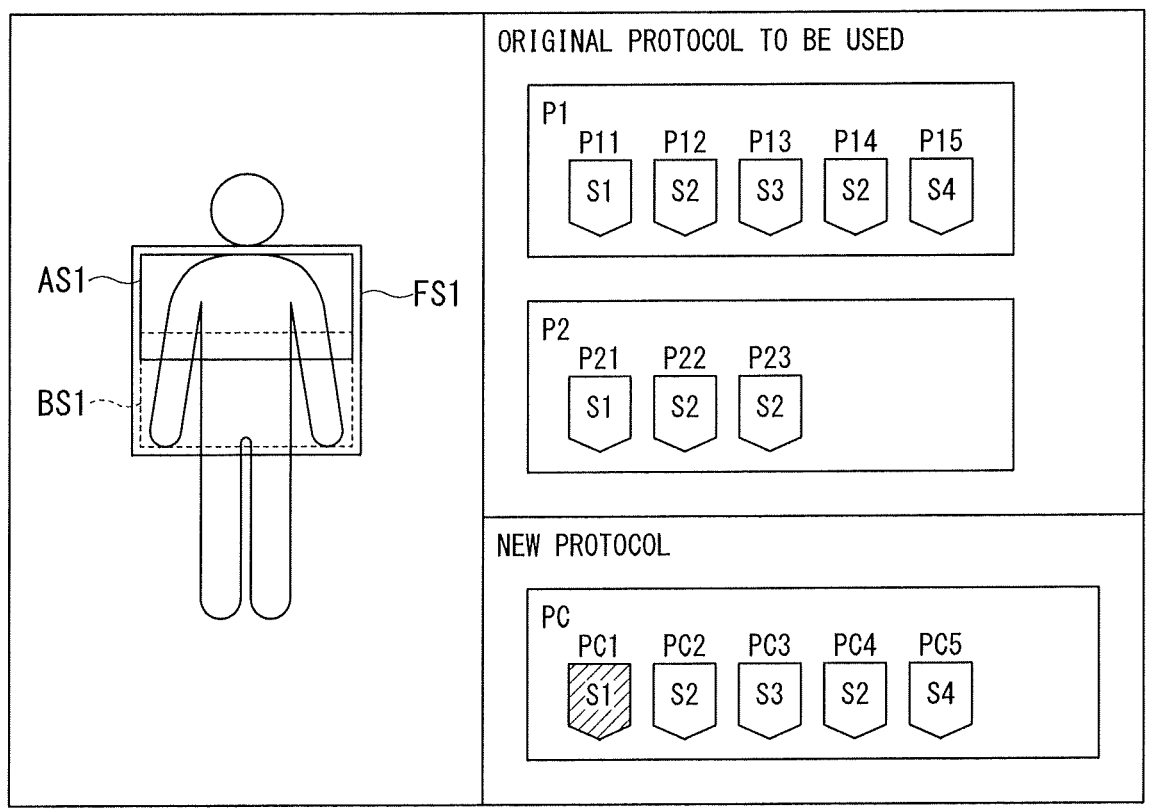
Figure 9:
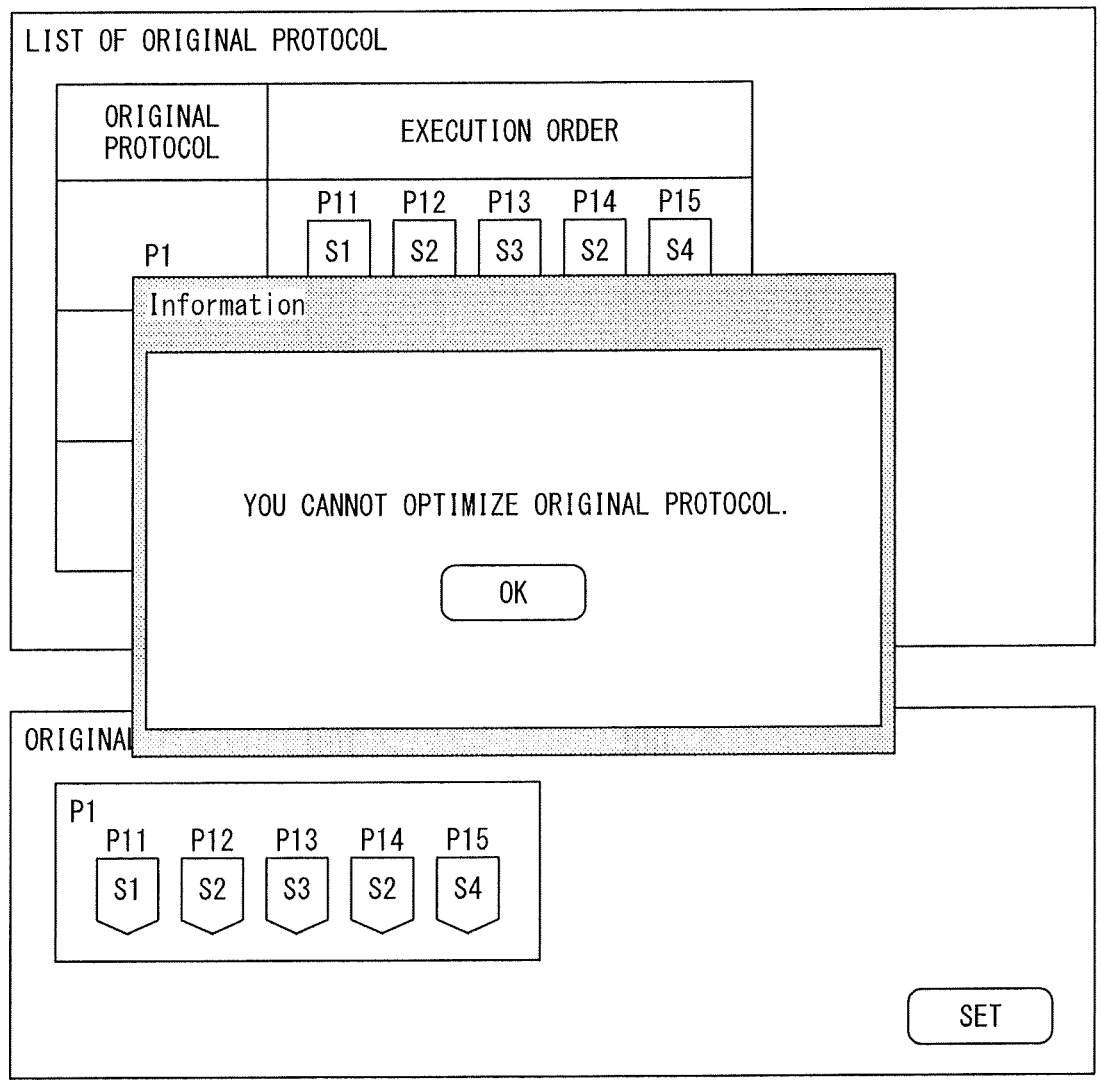
Figure 10:
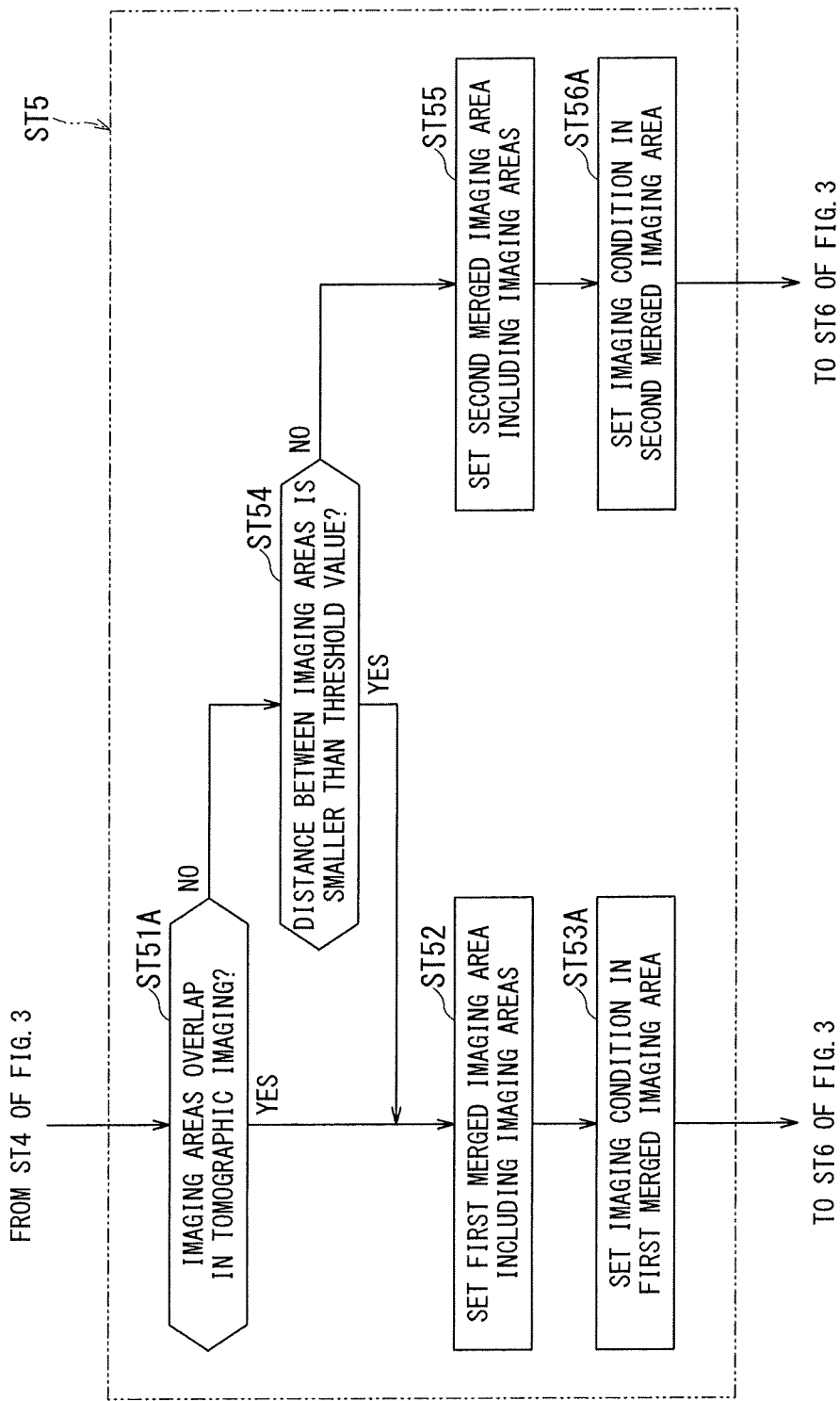
Figure 11:
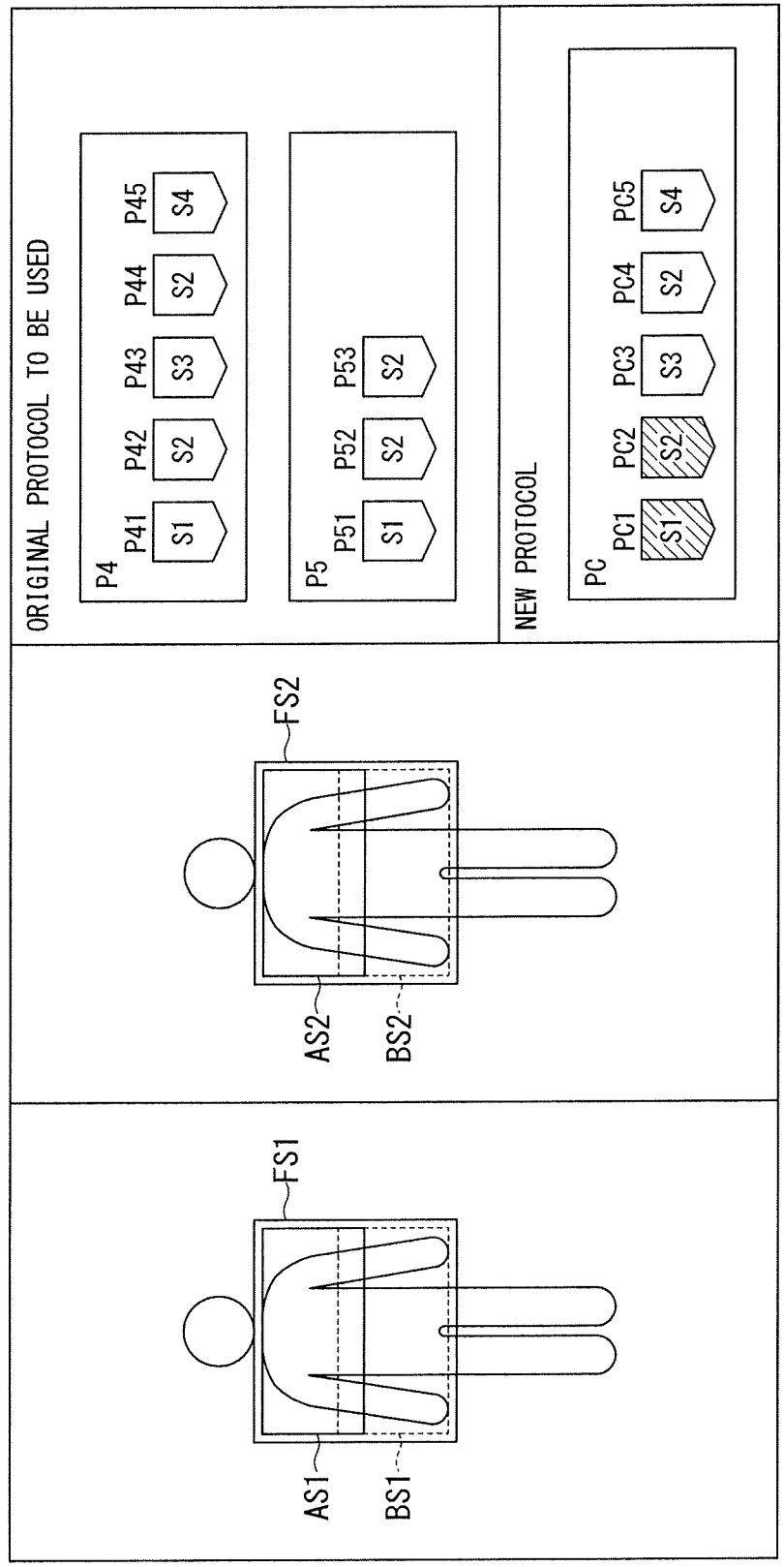
Figure 12:
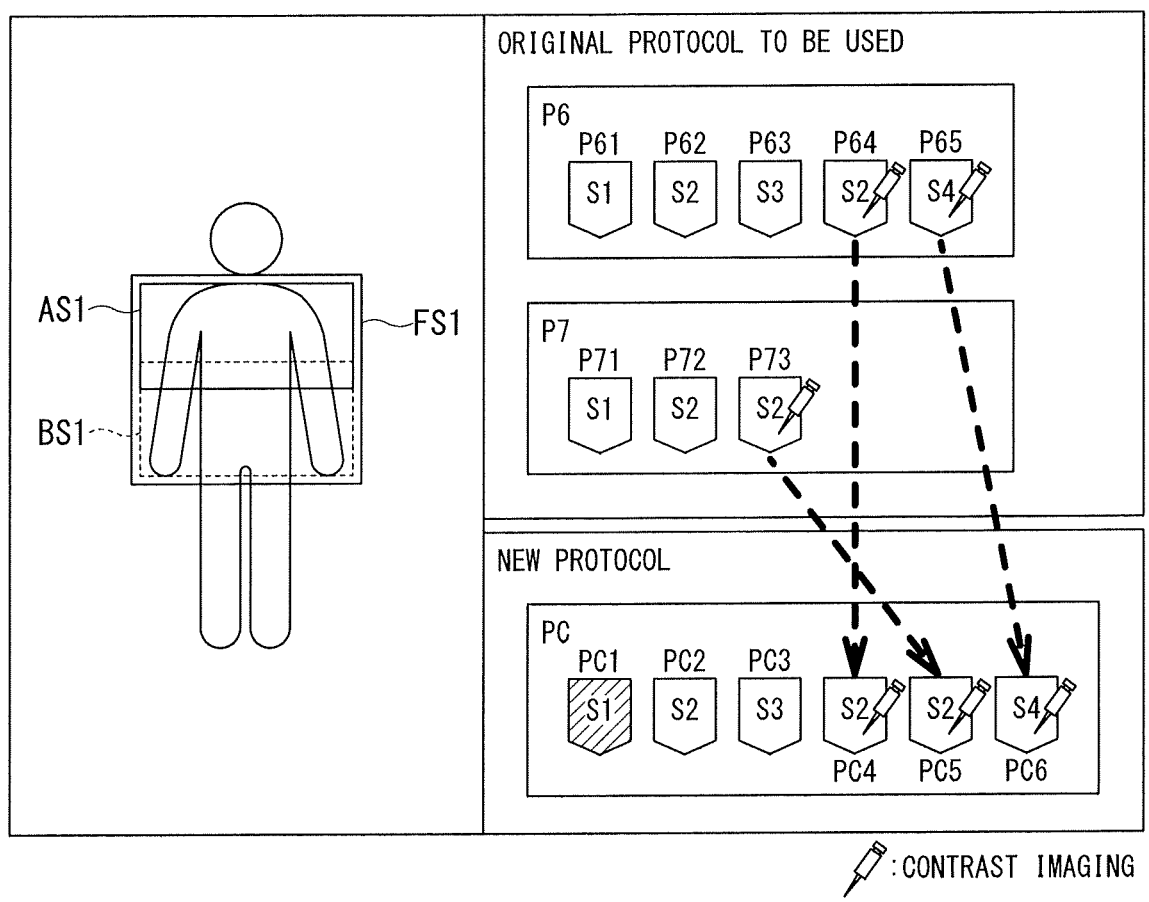
Figure 13:
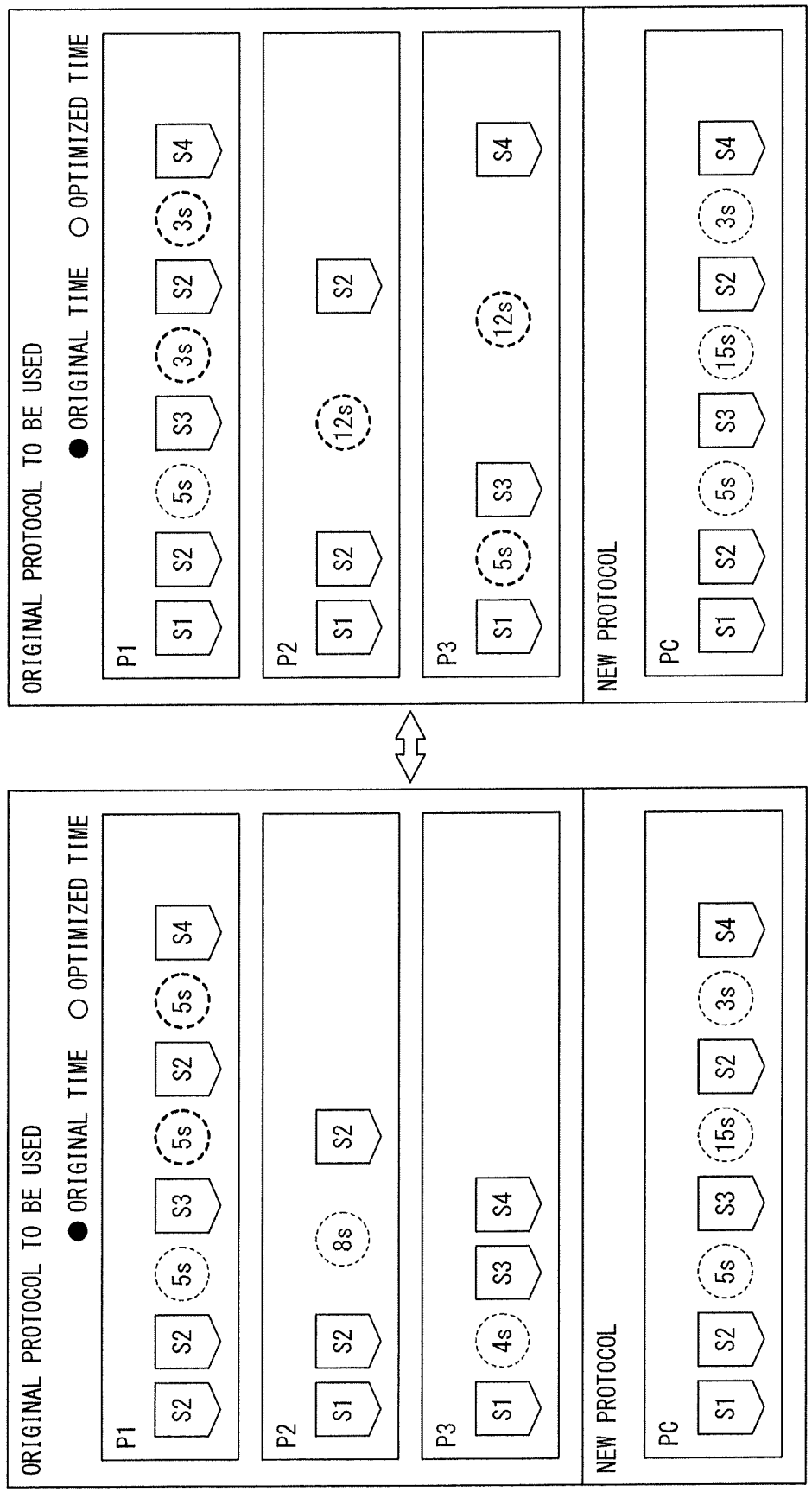
Figure 14:
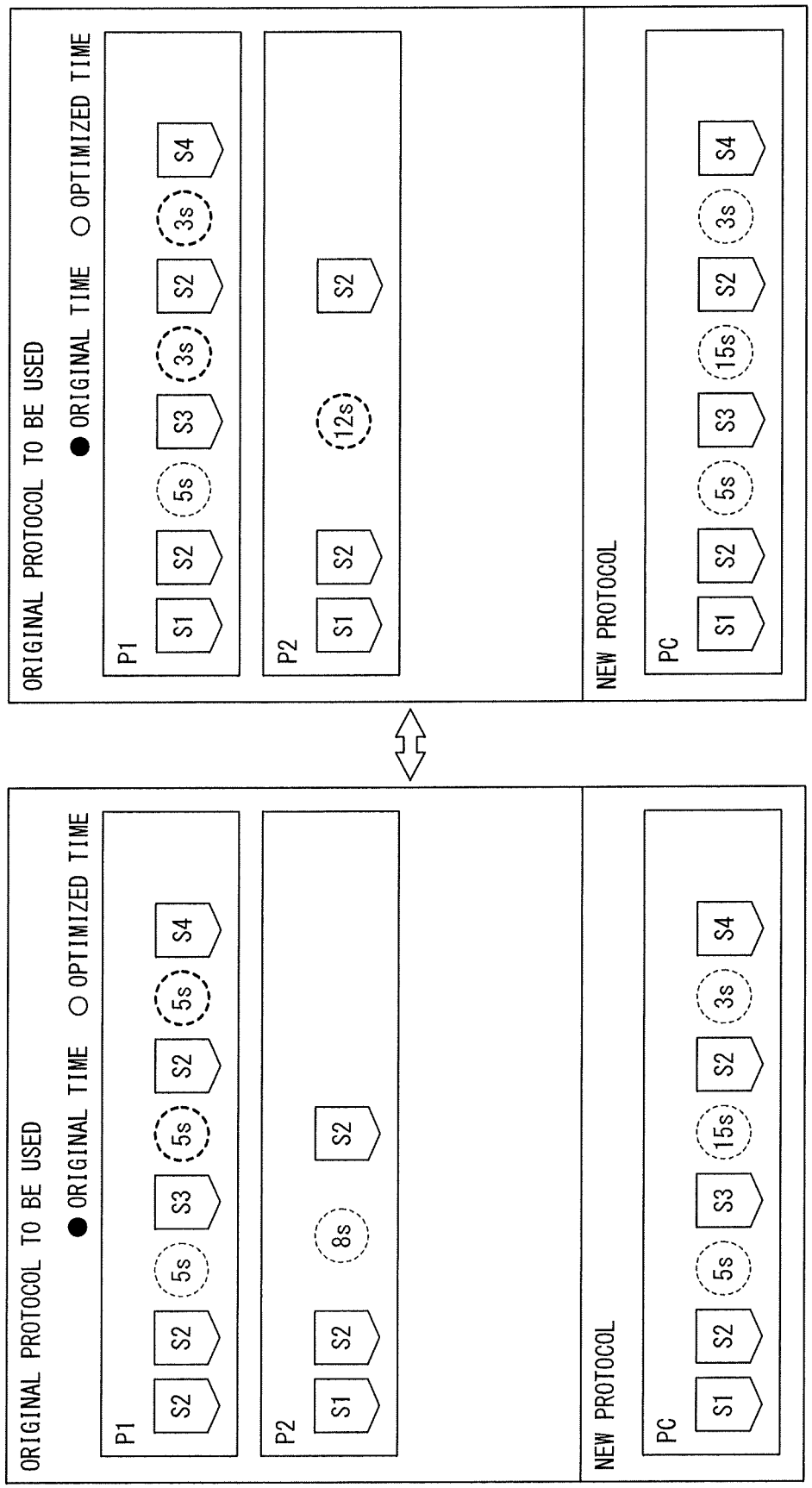

Each of FIGS. 7A to 7C is a diagram showing a relationship among imaging areas, in the X-ray CT apparatus according to the embodiment;

FIG. 8 is a diagram showing an example of a display screen of the new protocol, in the X-ray CT apparatus according to the embodiment;

FIG. 9 is a diagram showing an example of a confirmation screen in the case where generation of the new protocol is impossible, in the X-ray CT apparatus according to the embodiment;

FIG. 10 is a flowchart showing an operation example of step ST5 illustrated in FIG. 3, in the X-ray CT apparatus according to the embodiment;

FIG. 11 is a diagram showing an example of a display screen of the new protocol, in the X-ray CT apparatus according to the embodiment;

FIG. 12 is a diagram showing an example of a display screen of the new protocol, in the X-ray CT apparatus according to the embodiment;

FIG. 13 is a diagram showing an example of a time interval edit screen;

FIG. 14 is a diagram showing an example of a time interval edit screen; and

Figure 15:
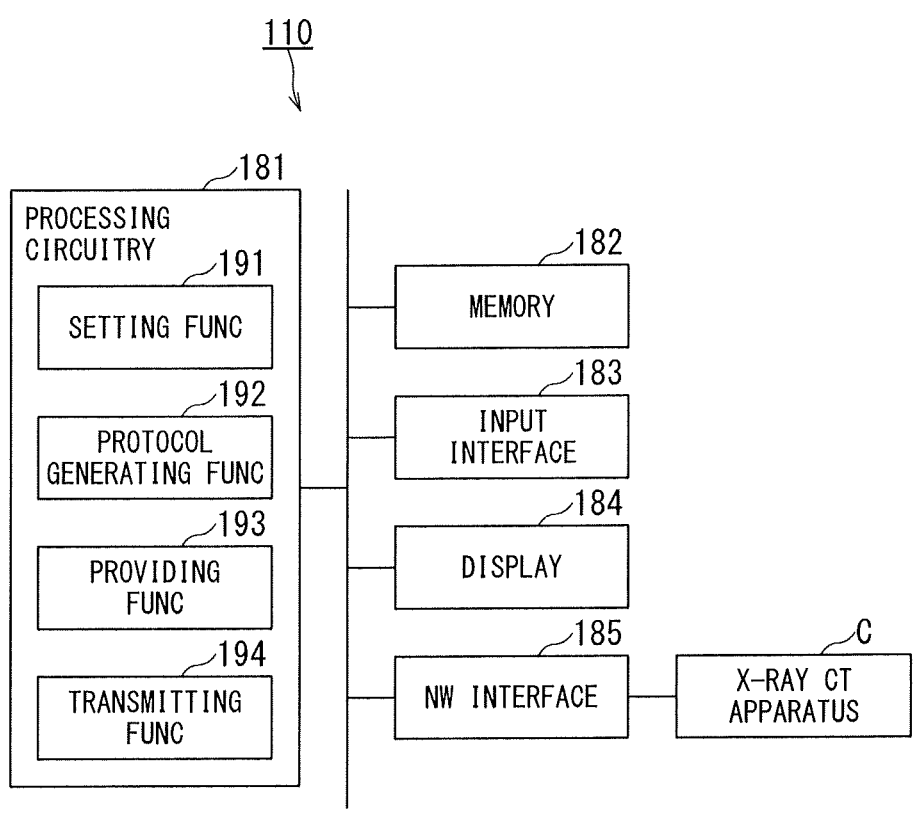

FIG. 15 is a block diagram showing an exemplary configuration and functions of an imaging management apparatus according to an embodiment.

DETAILED DESCRIPTION

An X-ray CT apparatus and an imaging management apparatus according to embodiments will be described in detail with reference to the drawings.

The X-ray CT apparatus according to the embodiment executes an imaging according to an imaging protocol including one or more image elements corresponding to an imaging type. The X-ray CT apparatus includes an X-ray source, an X-ray detector and processing circuitry. The X-ray source radiates an X-ray. The X-ray detector detects the X-ray. The processing circuitry merges, when first and second imaging protocols are set, first and second imaging elements, respectively included in the first and second imaging protocols, corresponding to same imaging type into a single third imaging element, thereby generating a third imaging protocol including the third imaging element.

1. X-Ray CT Apparatus

Data collection system based on an X-ray CT apparatus includes variations such as an R-R (Rotate/Rotate) system in which an X-ray tube and an X-ray detector rotate integrally around an object, and an S-R (Stationary/Rotate) system in which a large number of detection elements are arrayed in a ring form and only the X-ray tube rotates around the object. The present invention is applicable to either of the systems. Hereinafter, the X-ray CT apparatus according to the present embodiment will be explained on an exemplary case in which a third generation R-R system which is currently in dominant use is adopted.

Figure 1:
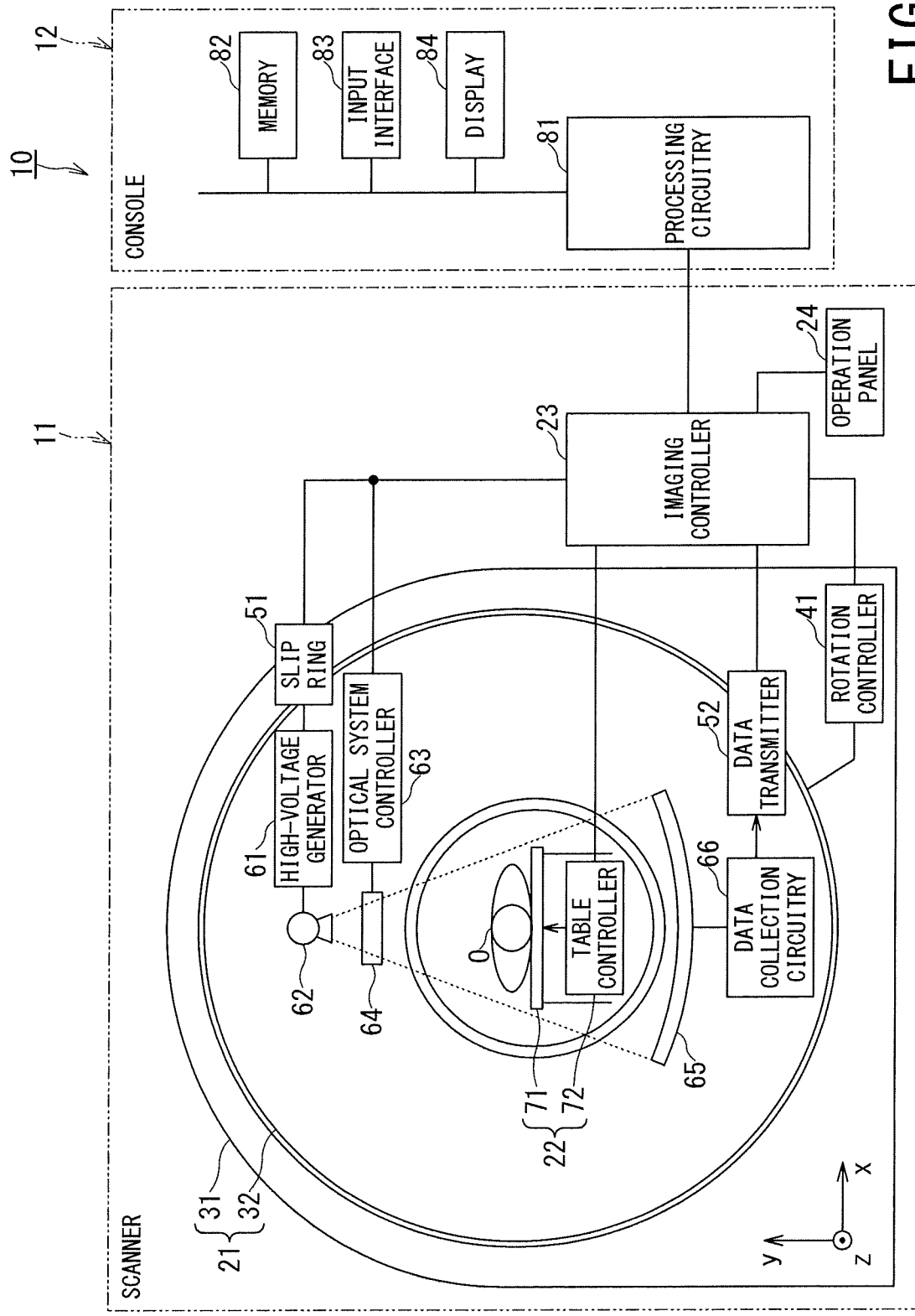
FIG. 1 is a diagram showing an exemplary configuration of an X-ray CT apparatus according to an embodiment.

FIG. 1 is a diagram showing an exemplary configuration of an X-ray CT apparatus according to an embodiment.

FIG. 1 shows an X-ray CT apparatus 10 according to the embodiment. The X-ray CT apparatus 10 includes a scanner 11 and a console 12. The console 12 is also referred to as an image processing apparatus. The scanner 11 of the X-ray CT apparatus 10 is typically installed in an examination room, and generates transmission data of X-rays relating to an object, for example, a patient O. On the other hand, the console 12, which is typically installed in a control room adjacent to the examination room, generates projection data based on the transmission data, and generates and displays an image such as a scanogram image or a tomographic image (reconstructed image).

The scanner 11 of the X-ray CT apparatus 10 includes a gantry 21, a bed 22, an imaging controller 23, and an operation panel 24.

The gantry 21 of the scanner 11 includes a fixed stand 31 fixed to a foundation part (not shown) and a rotator 32.

The fixed stand 31 includes a rotation controller 41. The rotation controller 41 has a mechanism for rotating the rotator 32 with respect to the fixed stand 31 under a control of the imaging controller 23 so as to rotate around an opening portion including a rotation center in a state where the rotator 32 maintains the positional relationship thereof.

The fixed stand 31 and the rotator 32 include a slip ring S1 and a data transmitter 52.

The slip ring 51 is a connector for rotating contact which allows passage of electric current while a brush such as a carbon brush and a wire brush on the side of the fixed stand 31 is pressed from sideward against a ring-shaped electric circuit (metal ring), which is disposed in a concentric manner with the rotator 32, so as to be allowed to slip to each other.

The data transmitter 52 includes a transmission circuit on the side of the rotator 32 and a reception circuit on the side of the fixed stand 31. The transmission circuit transmits raw data generated by data acquisition circuitry 66 to be described below to the reception circuit in a non-contact manner. The reception circuit provides the raw data transmitted from the transmission circuit to the imaging controller 23 to be described later.

The rotator 32 includes a high-voltage generator 61, an X-ray source (for example, X-ray tube) 62, an optical system controller 63, an X-ray optical system 64, an X-ray detector 65, and data acquisition circuitry 66. The rotator 32 is also called a rotatable frame. The rotator 32 holds components 61 to 66 integrally. That is, the rotator 32 can rotate integrally around the patient O with the X-ray tube 62 and the X-ray detector 65 being faced to each other. It is noted that a direction parallel with the central axis of rotation of the rotator 32, that is a longitudinal direction of a table 71, is defined as a z direction, and the plane orthogonal to the z direction is defined as an X direction and a y direction.

The high-voltage generator 61 provides power needed for executing various imaging to the X-ray tube 62 according to a control signal by the imaging controller 23 via the slip ring 51.

The X-ray tube 62 generates X-rays by causing an electron beam to collide with a target made of metal according to the tube voltage provided from the high-voltage generator 61, and radiates the X-rays toward the X-ray detector 65. A fan beam X-ray, a cone beam X-ray, and the like are formed by the X-rays radiated from the X-ray tube 62. The X-ray tube 62 is provided with power needed for radiation of X-rays through the control by the imaging controller 23.

The optical system controller 63 adjusts the irradiation range in the slice direction of X-rays in the X-ray optical system 64 through a control by the imaging controller 23.

The X-ray optical system 64 includes various instruments for controlling the radiation dose, irradiation range, shape, and radiation quality of X-ray beams. Specifically, the X-ray optical system 64 includes a wedge filter and a collimator. The wedge filter adjusts the X-ray dose of the X-rays generated at the X-ray tube 62. The collimator is a slit for reducing the irradiation range of X-rays for the X-rays of which radiation dose has been adjusted through the control by the optical system controller 63. The X-ray detector 65 is a detector of one-dimensional array type which has detection elements in the channel direction and a single detection element in the row (slice) direction. Alternatively, the X-ray detector 65 is a detector of matrix type, that is, of two-dimensional array type which has detection elements in the channel direction and detection elements in the slice direction. The X-ray detector 65 detects X-rays radiated from the X-ray tube 62.

The detector of two-dimensional array type is also called a multi-slice type detector. When the X-ray detector 65 is a multi-slice type detector, it is possible to perform an imaging of a 3-dimensional range having a width in the row direction by one rotation (or a half rotation+α) of the rotator 32, that is a volume imaging.

The data acquisition circuitry 66 has DASs (Data Acquisition Systems). Each DAS performs data collection. Each DAS amplifies the signal of transmission data detected by each detection element of the X-ray detector 65, and transforms it into raw data which is a digital signal. Each DAS sends the raw data to the image controller 23 via the data transmitter 52.

The bed 22 of the scanner 11 includes a table 71 and a table controller 72. The table 71 can place a patient O thereon.

The table controller 72 includes a mechanism to cause the table 71 to move up and down along the y direction, and to enter/retreat in the z direction through the control by the imaging controller 23. The table controller 72 causes the patient O placed on the table 71 to be inserted toward the opening portion including the rotational center of the rotator 32, and causes the patient O placed on the table 71 to retreat from the opening portion.

The imaging controller 23 includes a central processing unit (CPU) not shown and a memory, etc. The imaging controller 23 controls the table controller 72 to prepare for an imaging in accordance with an instruction from the operation panel 24. The imaging controller 23 controls the rotation controller 41, the high-voltage generator 61, the optical system controller 63, etc. in accordance with an instruction from the console device 12 to execute the imaging according to an original protocol or a new protocol to be described later.

Here, the original protocol is preliminarily registered, and includes original elements corresponding to one or more imaging types in one examination, and an execution order of the original elements. That is, in different original protocols, the included imaging type or the execution order of the original elements are different. Examples of the original protocols include a head slice protocol, a head helical protocol, an electrocardiographic synchronization protocol, a chest helical protocol, a lower limb helical protocol, a lower extremity contrast protocol, an abdominal helical protocol, and an abdominal contrast protocol. These various original protocols are represented by reference numerals P1 to P3 in FIG. 4 to be described later.

Examples of the imaging type include a scanogram imaging, a non-helical imaging, and a helical imaging. The non-helical imaging is also called a conventional imaging. The non-helical imaging and the helical imaging are also referred to as a tomographic imaging requiring an image reconstruction. These imaging may include not only a data acquisition by irradiation with the X-rays but also a processing of reconstructing the acquired data. The imaging type is represented by reference numerals S1 to S4 in FIG. 4 to be described later.

The scanogram imaging is an imaging for positioning performed prior to other imaging. The scanogram imaging is performed with the position of the table 71 in the z direction fixed, by irradiating the X-rays at one rotation position while stopping the rotation of the rotator 32 and while moving the gantry 21 in the z direction. Alternatively, the scanogram imaging is performed with the position of the gantry 21 in the z direction fixed, by irradiating the X-rays at one rotation position while stopping the rotation of the rotator 32 and while moving the table 71 in the z direction.

The non-helical imaging as the tomographic imaging is performed with the position of the gantry 21 and the table 71 in the z direction fixed, by irradiating the X-rays at rotation positions while rotating the rotator 32. The non-helical imaging includes a slice imaging for acquiring one cross-section image in one rotation (or half rotation+a) of the rotator 32 or a volume imaging for acquiring cross-section images in one rotation (or half rotation+a) etc.

The helical imaging as the tomographic imaging is performed with the position of the table 71 in the z direction fixed, by irradiating the X-rays at rotation positions while rotating the rotator 32 and while moving the gantry 21 in the z direction. Alternatively, the helical imaging is performed with the position of the gantry 21 in the z direction fixed, by irradiating the X-rays at rotation positions while rotating the rotator 32 and while moving the table 71 in the z direction.

The operation panel 24, which is provided on both sides or in the front and rear of the opening portion of the gantry 21, accepts operations which the operator performs while confirming the status of the patient O. Specifically, it accepts an instruction of turning on or off a projector (not shown) for emitting light with which the operator visually confirms a detection range, and instructions of moving, stopping, and automatically feeding the table 71.

The console 12, which is composed based on a computer, can mutually communicate with external apparatuses via a network such as a local area network (LAN). The console 12 is made up of basic hardware elements such as processing circuitry 81, a memory (or storage) 82, an input interface 83, and a display 84. The processing circuitry 81 is interconnected with each hardware component, which constitutes the console 12, via a bus as a common signal transmission line. It is noted that the console 12 may include a storage medium drive.

The processing circuitry 81 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 81 reads programs stored in the memory circuitry 82 or directly implemented in the processing circuitry 81 and executes these programs to achieve the following functions.

The processing circuitry 81 may be a single processing circuit or a combination of multiple processing circuit elements. In the latter case, the memory 82 includes multiple memory elements each storing an element of a program, each of the multiple memory elements is provided for each of the multiple processing circuit elements. Alternatively, the memory 82 includes a single memory storing the program, the single memory is provided for the multiple processing circuit elements.

The memory 82 is made up of semiconductor memory devices such as a RAM (Random Access Memory) and a flash memory, hard discs, optical discs, and the like. The memory 82 may be made up of portable media such as a USB (Universal Serial Bus) memory and a DVD (Digital Video Disk). The memory 82 stores various processing programs (including application programs, as well as an OS (Operating System)) used in the processing circuitry 81, data necessary for executing the programs, and image data. Moreover, the OS may include a graphic user interface (GUI) which frequently uses graphics for displaying information for the operator on the display 84, and allows basic operations to be performed by use of the input interface 83.

The input interface 83 is a circuit for receiving input of a signal from an input device such as a pointing device which can be operated by the operator. Here, it is assumed that the input device itself is included in the input interface 83. When the input device is operated by the operator, the input interface 83 generates a signal corresponding to the operation and outputs it to the processing circuitry 81. It is noted that the console 12 may include a touch panel in which an input device is integrated with the display 84.

The display 84 is a display device such as a liquid crystal display panel, a plasma display panel, and an organic EL (Electro Luminescence) panel. The display 84 displays image data according to control by the processing circuitry 81.

Note that the console 12 may include a communication control circuit that is an interface (IF) configured by a connector conforming to a parallel connection specification or a serial connection specification. The communication control circuit transmits and receives, when the X-ray CT apparatus 10 is provided on the network, information to and from external devices on the network. For example, the communication control circuit transmits image data, generated by the X-ray CT apparatus 10, to an external device such as an image managing device or a diagnostic terminal (not shown), and performs a communication operation with the external device.

Figure 2:
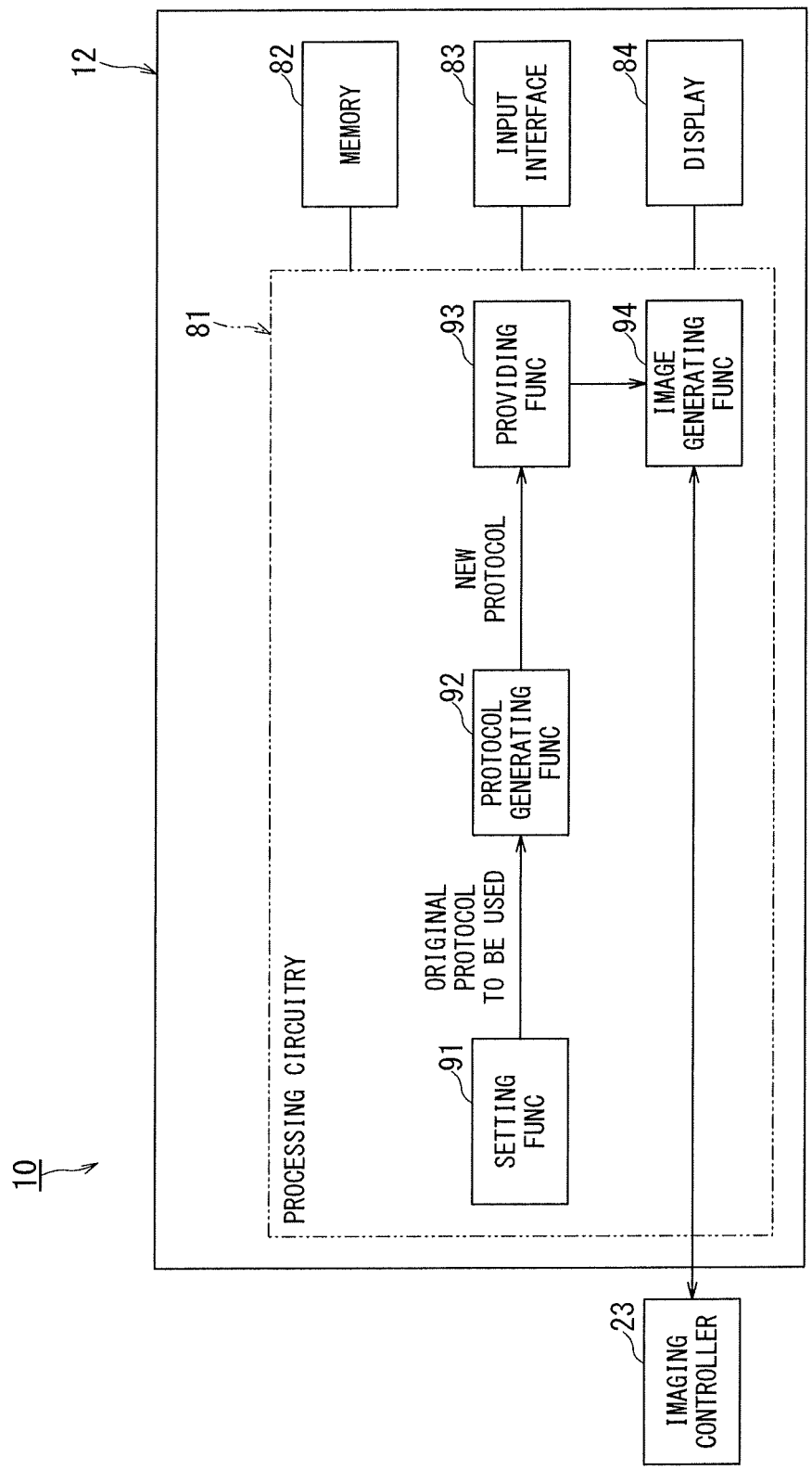
FIG. 2 is a block diagram showing functions of the X-ray CT apparatus according to the embodiment.

FIG. 2 is a block diagram showing functions of the X-ray CT apparatus.

When the processing circuitry 81 of the console 12 executes the program, as shown in FIG. 2, the X-ray CT apparatus 10 achieves a setting function (setting unit) 91, a protocol generating function (protocol generating unit) 92, a providing function (providing unit) 93, and an image generating function (image generating unit) 94. All or part of the functions 91 to 94 may be achieved by a circuit such as the ASIC included in the console 12. All or part of the functions 91 to 94 may be included not only in the console 12 but also in the imaging controller 23.

The setting function 91 is a function of setting, in a scan plan, an original protocol to be used, out of original protocols preliminarily registered. Here, the original protocol includes data on original elements corresponding to one or more imaging types in one examination, and an execution order of the original elements.

The protocol generating function 92 is a function of merging, when the original protocols are set by the setting function 91 in the scan plan, original elements corresponding to same imaging type into a single imaging element (hereinafter referred to as "merged element"), thereby generating a new imaging protocol (hereinafter referred to as "new protocol") including the merged element. The original elements corresponding to the same imaging type is included in the set original protocols. The protocol generating function 92 may generate the new protocol, in the scan plan, to include not only the merged element but also an original element not corresponding to the same imaging type. In that case, the protocol generating function 92 may include a function of organizing an execution order of the merged element etc., thereby generating a new protocol.

The protocol generating function 92 may organize, when one original imaging protocol is set by the setting function 91 in the scan plan, an execution order of original elements included in the set one original protocol, thereby generating a new protocol.

The providing function 93 is a function of providing, in the scan plan, an operator with the new protocol generated by the protocol generating function 92. For example, the providing function 93 displays the new protocol on the display 84.

The image generating function 94 is a function of setting, in the scan plan, imaging conditions for each imaging element included in the new protocol. An example of the imaging condition includes an X-ray irradiation condition, a field of view (FOV), a slice thickness, and the like. Here, there are cases where the imaging conditions include a moving speed and the like regarding the movement of the table 71 (or the gantry 21) in the z direction and the like.

The X-ray irradiation condition includes parameters related to X-rays to be irradiated. This parameters include, for example, a tube current mA, a tube voltage kV, an X-ray intensity control condition (modulation condition), a rotation speed of the rotator 32, an interval of helical imaging, a rotation speed of the rotator 32, a focus size of the X-ray tube 62 and the like relating to the irradiated X-ray. The parameters related to the field of view include control parameters related to the operation of the collimator of the X-ray optical system 64.

The image generating function 94 is a function of controlling the X-ray tube 62, the X-ray detector 65 and the like via the imaging controller 23, thereby executing the imaging elements included in the new protocol generated by the protocol generating function 92 in the order of execution thereof, and generating images such as a scanogram image and a tomographic image.

As an image reconstruction method for generating the tomographic image, an analytical method typified by convolution correction back projection (CBP) method or filtered back projection (FBP) method, and algebraic method are known. The image generating function 94 utilizes these methods. The algebraic method is generally called an iterative reconstruction (IR) method because the tomographic image is obtained using an iterative method.

Further, the image generating function 94 is a function of displaying the generated image on the display 84.

The specific operation of the functions 91 to 94 will be described later.

FIG. 3 is a flowchart showing an operation example of the X-ray CT apparatus 10.

As shown in FIG. 3, in the scan plan, the setting function 91 sets an original protocol to be used, out of original protocols preliminarily registered (step ST1).

FIG. 4 is a diagram showing an example of a setting screen of the original protocol to be used.

The upper part of FIG. 4 shows three original protocols preliminarily registered. Three original protocols P1 to P3 are shown as examples of three original protocols preliminarily registered. The original protocol P1 includes five original elements corresponding to four imaging types, and an execution order of the five original elements. That is, the original protocol P1 includes five original elements P11 to P15 corresponding to the four imaging types S1 to S4, and their execution order as P11, P12, P13, P14 and P15.

The original protocol P2 includes three original elements corresponding to two imaging types, and an execution order of the three original elements. That is, the original protocol P2 includes three original elements P21 to P23 corresponding to the two imaging types S1 and S2, and their execution order as P21, P22 and P23.

The original protocol P3 includes three original elements corresponding to three imaging types, and an execution order of the three original elements. That is, the original protocol P3 includes three original elements P31 to P33 corresponding to the three imaging types S1, S3 and S4, and their execution order as P31, P32 and P33.

The operator operates the input interface 83 to select two original protocols P1 and P2 out of the three original protocols P1 to P3 on the upper part of the setting screen. The lower part of FIG. 4 shows the two selected original protocols P1 and P2. The setting function 91 sets, when the operator operates the input interface 83 to press the "set" button on the setting screen, the two selected original protocols P1 and P2 as original protocols to be used.

Here, the operator can operate, when the operator selects "head helical protocol" as the original protocol to be used, the input interface 83, thereby first selecting an imaging part "head", and secondly selecting "helical imaging" out of the imaging type "tomographic imaging" corresponding to the imaging part. Alternatively, the operator can operate, when the operator selects "head helical protocol" as the original protocol to be used, the input interface 83, thereby directly selecting "head helical imaging" as the original protocol to be used, out of the original protocols.

Returning to the explanation of FIG. 3, the protocol generating function 92 determines, in the scan plan, whether or not there are original protocols to be used set in step ST1 (step ST2). If it is determined as "YES" in step ST2, that is, if it is determined that there are original protocols to be used, the protocol generating function 92 determines, in the scan plan, whether or not there is same imaging type in the original protocols to be used set in step ST1 (step ST3).

For example, in step ST3, the protocol generating function 92 determines whether or not there are scanogram imagings as the same imaging type in the two original protocols to be used, respectively.

If it is determined as "YES" in step ST3, that is, if it is determined that there is same imaging type in the original protocols to be used, the protocol generating function 92 determines, in the scan plan, whether or not to generate a new protocol. That is, the protocol generating function 92 determines whether to optimize the original protocol or not (step ST4).

Figure 5:
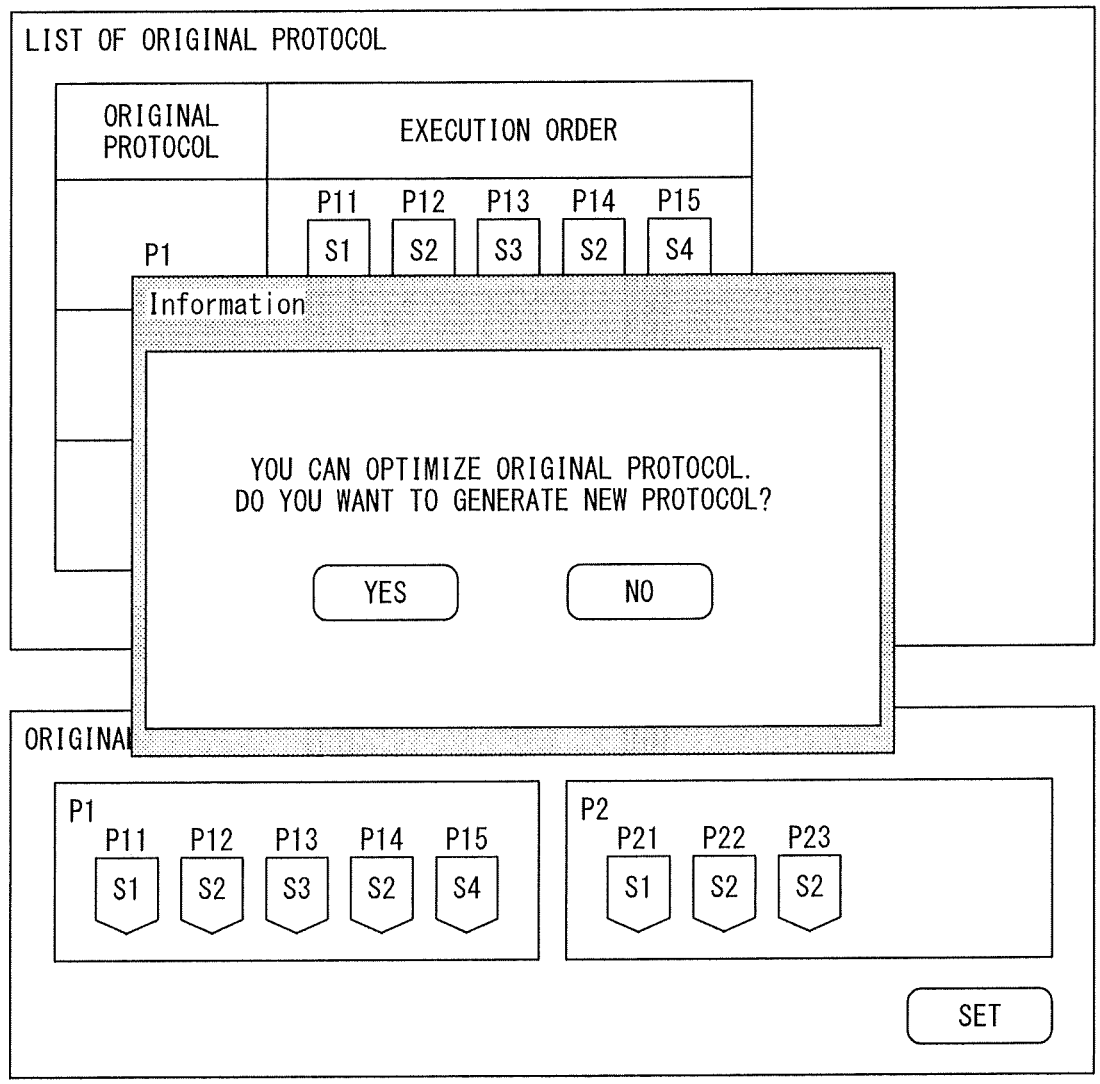
FIG. 5 is a diagram showing an example of a selecting screen as to whether or not to generate a new protocol, in the X-ray CT apparatus according to the embodiment.

FIG. 5 is a diagram showing an example of a selecting screen as to whether or not to generate the new protocol.

As the selecting screen shown in FIG. 5, for example, a message box arranged on an upper layer of the setting screen shown in FIG. 4 can be used.

When a "set" button is pressed on the setting screen shown in FIG. 4 and when both of the two original protocols to be used include the scanogram imaging, the message box shown in FIG. 5 is displayed. The protocol generating function 92 determines, when the operator presses the "Yes" button of the message box by operating the input interface 83, to generate the new protocol. In that case, five imaging elements PC1 to PC5 corresponding to the four imaging types S1, S2, S3 and S4 included in the new protocol PC shown in FIG. 8 can be executed in that order.

The protocol generating function 92 determines, when the operator presses the "NO" button of the message box by operating the input interface 83, not to generate the new protocol. In that case, as shown in the lower part of FIG. 4, imaging conditions are set for each original element included in the original protocol P1, and five imagings corresponding to five original elements P11 to P15 related to the original protocol P1 are sequentially executed. Then, imaging conditions are set for each original element included in the original protocol P2, and three imagings corresponding to three original elements P21 to P23 related to the original protocol P2 are sequentially executed.

Returning to the explanation of FIG. 3, if it is determined as "YES" in step ST4, that is, if it is determined to generate the new protocol, the protocol generating function 92 merges the original elements corresponding to the same imaging type, which are determined to exist in step ST3, thereby generating a simple new protocol (step ST5), and then, organizes an execution order (step ST6). By the steps ST5 and ST6, the new protocol is generated. The organization by step ST6 is not indispensable.

Figure 6:
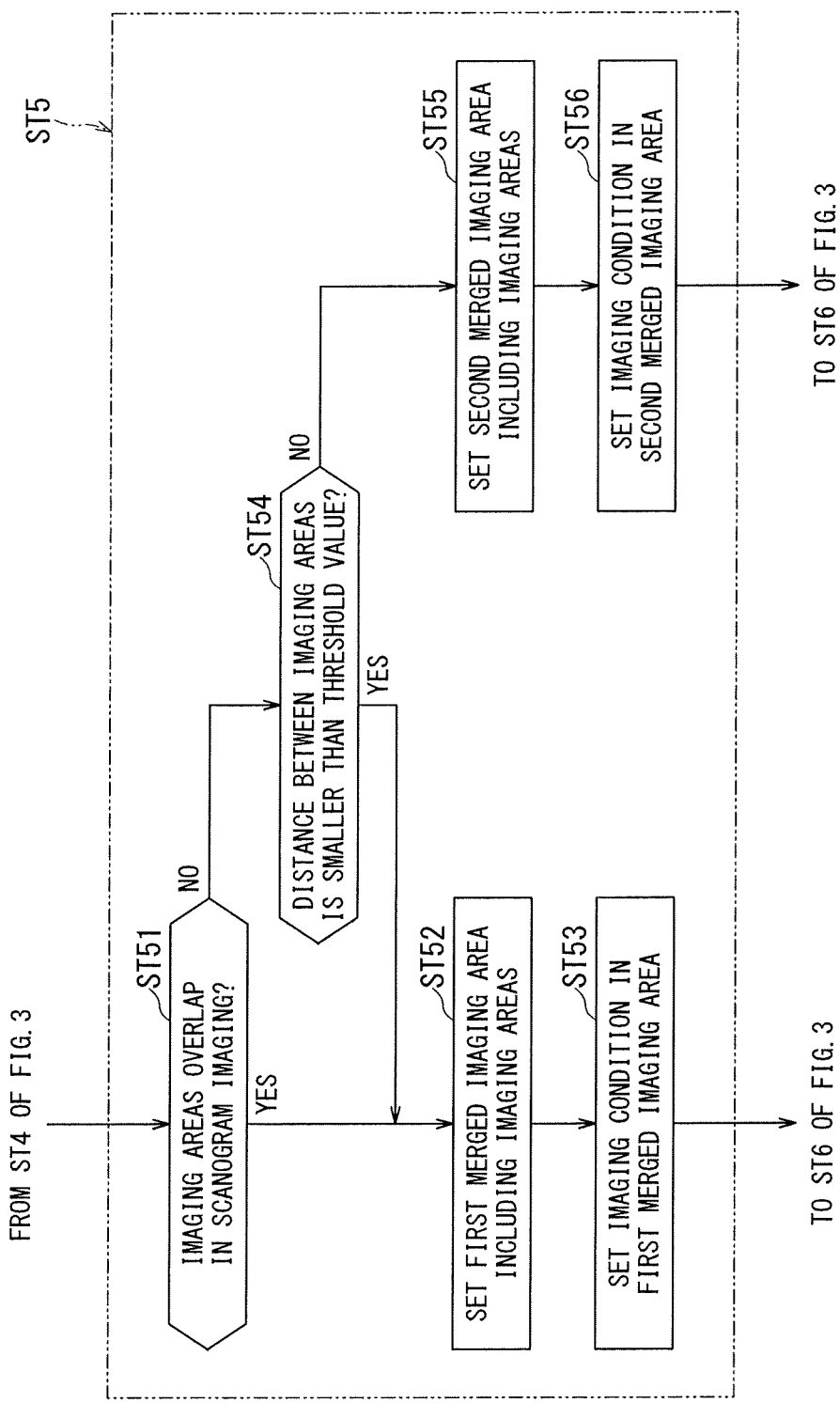
FIG. 6 is a flowchart showing an operation example of step ST5 illustrated in FIG. 3, in the X-ray CT apparatus according to the embodiment.

FIG. 6 is a flowchart showing an operation example of step ST5 illustrated in FIG. 3.

FIG. 6 shows a case where two original protocols to be used include a scanogram imaging as the same imaging type, and shows a case where it is determined in step ST4 to generate the new protocol by merging original protocols related to the scanogram imaging.

The protocol generating function 92 determines whether there is an overlapping of the imaging areas in the scanogram imaging as the same imaging type (step ST51). If it is determined as "YES" in the determination in step ST51, that is, if it is determined that there is the overlapping of the imaging areas in the scanogram imaging, the protocol generating function 92 sets an area including the imaging areas as a first merged imaging area including only X-ray irradiation area (step ST52). The protocol generating function 92 sets an imaging condition in the first merged imaging area set in step ST52 (step ST53), and proceeds to step ST6 shown in FIG. 3.

FIG. 7A is a diagram showing the overlapping of the imaging areas.

As shown in FIG. 7A, the overlapping occurs between the imaging area AS1 of the original element P11, corresponding to the scanogram imaging S1 of the original protocol P1, and the imaging area BS1 of the original element P21, corresponding to the scanogram imaging S1 of the original protocol P2. When the overlapping occurs between the imaging area AS1 and the imaging area BS1, the area including the imaging areas AS1 and BS1 is set as the first merged imaging area FS1 including only the X-ray irradiation area.

Returning to the explanation of FIG. 6, if it is determined as "NO" in step ST51, that is, if it is determined that there is no overlapping of the imaging areas in the scanogram imaging, the protocol generating function 92 determines whether a distance between the imaging areas is smaller than a threshold or not (step ST54). If it is determined as "YES" in step ST54, that is, if it is determined that the distance of the non-overlapping imaging areas are smaller than the threshold value, the protocol generating function 92 sets an area including the imaging areas and an area therebetween as a first merged imaging area including only the X-ray irradiation area (step ST52), and sets an imaging condition in the first merged imaging area set in step ST52 (step ST53).

FIG. 7B is a diagram showing a case where the distance between two non-overlapping imaging areas is smaller than the threshold value.

As shown in FIG. 7B, the distance d occurs between the imaging area AS1 of the original element P11, corresponding to the scanogram imaging S1 of the original protocol P1, and the imaging area BS1 of the original element P21, corresponding to the scanogram imaging S1 of the original protocol P2. When the interval d is smaller than the threshold value, the area including the imaging areas AS1 and BS1 and the area therebetween is set as the first merged imaging area FS1.

Returning to the explanation of FIG. 6, if it is determined as "NO" in step ST54, that is, if it is determined that the distance between the non-overlapping imaging areas is equal to or larger than the threshold value, the protocol generating function 92 generates the imaging areas and an area therebetween as a second merged imaging area including the X-ray irradiation area and a non-irradiation area (step ST55). The protocol generating function 92 sets an imaging condition in the second merged imaging area (step ST56), and proceeds to step ST6 shown in FIG. 3.

FIG. 7C is a diagram showing a case where the distance between the non-overlapping imaging areas is equal to or larger than the threshold value.

As shown in FIG. 7C, the distance e occurs between the imaging area AS1 of the original element P11, corresponding to the scanogram imaging S1 of the original protocol P1, and the imaging area BS1 of the original element P21, corresponding to the scanogram imaging S1 of the original protocol P2. When the interval e is equal to or larger than the threshold value, the area including the imaging areas AS1 and BS1 and the area therebetween is set as the second merged imaging area GS1 including the X-ray irradiation area and the non-irradiation area.

The second merged imaging area GS1 includes the imaging areas AS1 and BS1 as the X-ray irradiation area, and the other area as the non-irradiation area. If it is determined that it is not preferable to continuously perform scanogram imagings, for example, in a case where imaging parts of the two scanogram imagings S1 and S2 are away, the second merged imaging area GS1 is set by threshold processing.

Returning to the explanation of FIG. 3, the providing function 93 displays, on the display 84, the new protocol including the merged element generated in step ST5 in the scan plan (step ST7).

FIG. 8 is a diagram showing an example of a display screen of the new protocol.

The upper right part of FIG. 8 shows two original protocols P1 and P2 to be used set on the setting screen shown in FIG. 4. By storing data of two original protocols P1 and P2 at the time of preset, it is possible to display two original protocols P1 and P2 on the display screen of the new protocol. For example, the new protocol PC may have a reference key indicating the two original protocols P1 and P2, or may have the two original protocols P1 and P2 in an independent state and store them together with a difference based on the optimization of the original protocols.

The lower right part of FIG. 8 shows the new protocol PC when the first merged imaging area FS1 is set based on the imaging areas AS1 and BS1 of the scanogram imaging S1. The new protocol PC includes five imaging elements corresponding to the four imaging types and an execution order of the five imaging elements. That is, the new protocol PC includes five imaging elements PC1 to PC5 corresponding to four imaging types S1 to S4, and their execution order as PC1, PC2, PC3, PC4 and PC5. Here, the imaging type S1

(hatched portion in the FIG. 8) of the new protocol PC corresponds to the merged element, and means the scanogram imaging associated with the first merged imaging area FS1. Further, one imaging type S2 included in the original protocol P1 and two imaging types S2 included in the original protocol P2 may be merged at once in the new protocol PC.

The left side of FIG. 8 shows the imaging areas AS1 and BS1 of the original elements P11 and P21 corresponding to the scanogram imaging S1 in the two original protocols P1 and P2 to be used. Here, the case of FIG. 7A will be described. The left side of FIG. 8 shows the first merged imaging area FS1 of the merged element PC1 corresponding to the scanogram imaging S1 in the new protocol PC. That is, the two original elements P11 and P21 are merged in the imaging area of the scanogram imaging S1.

With the display screen of the new protocol shown in FIG. 8, the operator can ascertain which the imaging type corresponding to the original element has been merged before and after generation of the new protocol, and the like. Also, after generation of the new protocol PC, the imaging can be executed on the original protocol basis ("NO" in step ST8 to be described later).

Further, a correspondence table between a combination of the original protocols and the generated new protocol may be newly registered, or the new protocol may be newly registered as an original protocol. In these cases, it is possible to simplify generation of the next new protocol. Furthermore, the generation of the new protocol can be performed not only at the time of the examination but also at the time of preset creation.

In this way, from the viewpoint of reducing exposure of the patient O, it is described that the original elements are merged by merging the imaging areas, but the present invention is not limited to that case. The protocol generating function 92 may select and set, in steps ST53 and ST56, an imaging condition of the merged element based on the imaging conditions relating to the original elements corresponding to the same imaging type, for example, presets of focus sizes, thereby merging the original elements. In this case, the operator may select merging of the imaging conditions or merging of the imaging areas.

The protocol generating function 92 may select and set, in steps ST53 and ST56, representative values, for example, the maximum value, the minimum value, and the average value of the imaging conditions preset corresponding to the original elements, as the imaging conditions of the merged element. The protocol generating function 92 may preferentially select and set, when priorities for selection setting are given in advance to the original protocols respectively in steps ST53 and ST56, an imaging condition of the preset possessed by an element of an original protocol with higher priority at the time of selection setting, as the imaging condition of the merged element. The protocol generating function 92 may select and set, when the imaging condition is the tube current in steps ST53 and ST56, tube currents preset corresponding to the original elements, respectively, in accordance with the imaging areas. This is to ensure image quality.

In addition, there may be a case where a merging method and an execution order are set so as to minimize the time (including waiting time between imagings) required for the whole of the imagings corresponding to the imaging elements included in the new protocol, that is the time required for the examination of the patient O. The execution order of the imaging elements may be set according to the priority of imaging execution. For example, when an imaging type (including reconstruction) performed for the purpose of screening for finding a patient with a specific disease is included, an imaging element corresponding to the imaging type is prioritized, and an imaging elements corresponding to the other imaging type that take time or an imaging type including processing requiring high load are postponed. Further, when the original protocol including the dual energy imaging which irradiates the X-rays having different energies is set as one of the original protocols to be used, display of a monochrome image is added, in step ST7, after generation of a tomographic image. That is, a confirmation display as to whether or not subtraction processing is to be added may be performed.

Returning to the explanation of FIG. 3, the operator operates the input interface 83 to select, in step ST7, the merged imaging type included in the new protocol, so that the protocol generating function 92 may manually release the merging. The operator operates the input interface 83 to select, in step ST7, the imaging types included in the original protocol, so that the protocol generating function 92 may manually merge the imaging types. The protocol generating function 92 may also display an error message if the operator cannot merge the imaging types selected by operating the input interface 83. In that case, if it is determined that the merging is possible between some of the imaging types, the protocol generating function 92 can also present the fact to the operator.

The image generating function 94 determines whether or not to execute the imaging elements (which may include the original elements in addition to the merged elements), included in the new protocol displayed in step ST7, according to the execution order thereof (step ST8). Here, the operator visually recognizes the new protocol generated according to the purpose of radiation reduction of the patient O, and can finally decide whether or not to perform the imaging with the new protocol.

If it is determined as "YES" in step ST8, that is, if it is determined that the imaging elements included in the displayed new protocol should be executed according to the execution order, the image generating function 94 sets a reconstruction condition for an imaging type, included in the new protocol, requiring reconstruction, that is, an imaging element corresponding to the tomographic imaging (step ST9). The reconstruction condition includes a reconstruction function and a reconstruction distance and the like. The original protocols to be used are optimized in steps ST5 and ST6, but the image generating function 94 can follow the reconstruction condition before merged.

Here, the image generating function 94 can reorganize, based on the reconstruction condition set in step ST9, the execution order of the imaging elements organized in step ST6. As reconstruction processing becomes more sophisticated, processing time may be required depending on imaging conditions in some cases, occupying the reconstruction unit, and it may take time to judge success or failure of the imaging. Therefore, the image generating function 94 reorganizes the execution order in the order of decreasing processing time in each of the imaging elements based on the reconstruction conditions set for each imaging type of the original protocol to be used.

The image generating function 94 controls the X-ray tube 62, the X-ray detector 65, and the like via the imaging controller 23 so as to sequentially perform the imagings corresponding to the imaging elements included in the new protocol in the execution order (step ST10).

Here, the imaging condition of the imaging element, included in the new protocol set in steps ST53 and ST56, can also be followed in the imaging element of the original protocol. It is possible to save all of the followed imaging conditions together with the new protocol or to save only an imaging condition selected by the operator out of the reflected imaging conditions.

The image generating function 94 generates an image such as the scanogram image and the tomographic image based on data acquired by the imaging according to the new protocol, and displays the image on the display 84 (step ST11).

The image generating function 94 may display, in step ST11, the image generated based on the imaging according to the new protocol on the display 84 in units of the original protocols to be used corresponding to the new protocol, or in unit of the new protocol. The former is realized by adding information on an original protocol corresponding to the new protocol, to an image or series generated according to the new protocol.

The image generating function 94 determines, in step ST11, relevance between images obtained by the imagings according to the new protocol, and groups images with high relevance, and displays them on the display 84 at the time of image interpretation. For example, in the case where the imaging protocol with non-contrast and the imaging protocol with contrast are set to be used at the same imaging part, the image generating function 94 determines that the image based on the non-contrast imaging protocol is an image group with high relevance to the image based on the contrast imaging protocol, and display them in parallel on the display 84.

If it is determined "NO" in steps ST2 and ST3, that is, if it is determined that generation of the new protocol is impossible, the image generating function 94 sets a reconstruction condition for an imaging type, included in the original protocol, requiring reconstruction, that is, an imaging element corresponding to the tomographic imaging (step ST12). The image generating function 94 controls the X-ray tube 62, the X-ray detector 65, and the like via the imaging controller 23 so as to sequentially perform the imagings corresponding to the imaging elements included in the original protocol in the execution order (step ST13).

FIG. 9 is a diagram showing an example of a confirmation screen in the case where generation of the new protocol is impossible.

FIG. 9 shows an example of a confirmation screen when optimization of the original protocols to be used cannot be performed, that is, generation of the new protocol is impossible. As the confirmation screen shown in FIG. 9, for example, a message box arranged on an upper layer of the setting screen shown in FIG. 4 can be used. An example of a case where the generation of the new protocol is impossible is a case where there is one original protocol to be used, as shown in FIG. 9.

Returning to the explanation of FIG. 3, the image generating function 94 generates an image based on data acquired by the imaging according to the original protocol, and displays the image on the display 84 (step ST11).

If it is determined "NO" in steps ST4 and ST8, that is, if it is determined that generation of the new protocol is impossible, the image generating function 94 sets a reconstruction condition for an imaging type, included in the original protocol, requiring reconstruction, that is, an imaging element corresponding to the tomographic imaging (step ST12). The image generating function 94 controls the X-ray tube 62, the X-ray detector 65, and the like via the imaging controller 23 so as to sequentially perform the imagings corresponding to the imaging elements included in the original protocol in the execution order (step ST13). The image generating function 94 generates an image based on data acquired by the imaging according to the original protocol, and displays the image on the display 84 (step ST11).

In the prior art, when original protocols are used, it is necessary to manually perform optimization of the imaging area or the like before execution of each original protocol. For that reason, time is required for optimization before each original protocol is executed, so there is a problem that the throughput of the whole examination is reduced. In addition, although it is possible to adopt a method of preliminarily registering conditions according to combinations of original protocols, conditions as many as the number of combinations are required, and it is difficult to increase the number of original protocols and to reuse the original protocol.

In the prior art, when original protocols are used and they are executed consecutively, imaging areas of the corresponding imaging types may overlap among the original protocols. In that case, unnecessary exposure occurs.

According to the X-ray CT apparatus 10, it is possible to freely generate the new protocol, corresponding to small X-ray exposure to the patient O, and provide the operator with the new protocol, since the same imaging type is specified based on the original protocols, and the imaging areas of the original elements corresponding to the same imaging type are merged. Further, according to the X-ray CT apparatus 10, it is possible to reduce the examination time, since the imaging conditions of the original elements corresponding to the same imaging type are optimized.

First Modified Example

As described above, in the case where the original protocols to be used include the scanogram imaging as the same imaging type, a method of generating a new protocol by merging the imaging areas of the scanogram imaging has been described. However, the imaging types that can be the same are not limited to the scanogram imaging. Hereinafter, a method of merging the imaging areas of the tomographic imaging (non-helical imaging or helical imaging) will be described.

FIG. 10 is a flowchart showing an operation example of step ST5 illustrated in FIG. 3.

FIG. 10 shows a case where two original protocols to be used include a tomographic imaging as the same imaging type, and shows a case where it is determined in step ST4 (shown in FIG. 3) to generate the new protocol by merging original protocols related to the tomographic imaging.

In FIG. 10, the same symbols are assigned to the same steps as those shown in FIG. 6. The description of these components is omitted.

The protocol generating function 92 determines whether there is an overlapping of the imaging areas in the tomographic imaging as the same imaging type (step ST51A). If it is determined as "YES" in the determination in step ST51A, that is, if it is determined that there is the overlapping of the imaging areas in the tomographic imaging, the protocol generating function 92 sets an area including the imaging areas as a first merged imaging area including only X-ray irradiation area (step ST52). On the other hand, if it is determined as "NO" in step ST51A, that is, if it is determined that there is no overlapping of the imaging areas in the tomographic imaging, the protocol generating function 92 determines whether a distance between the imaging areas is smaller than a threshold or not (step ST54).

In this way, the imaging areas of the tomographic imaging, which are related to different original protocols and are individually executed at different timings, are summarized, therefore the new protocol is generated which is executed as a series of imaging.

The protocol generating function 92 sets an imaging condition in the first merged imaging area (step ST53A). The protocol generating function 92 can set the imaging condition (for example, X-ray irradiation conditions) with appropriate helical pitch and beam pitches so that images of the imaging areas (imaging parts) can maintain optimum image quality.

FIG. 11 is a diagram showing an example of a display screen of the new protocol.

The upper right part of FIG. 11 shows two original protocols P4 and P5 to be used. The lower right part of FIG. 11 shows the new protocol PC when the first merged imaging area FS1 is set based on the imaging areas AS1 and BS1 of the scanogram imaging S1, and when the first merged imaging area FS2 is set based on the imaging areas AS2 and BS2 of the non-helical imaging S2 of the tomographic imaging.

The new protocol PC includes five imaging elements corresponding to the four imaging types and an execution order of the five imaging elements. That is, the new protocol PC includes five imaging elements PC1 to PC5 corresponding to four imaging types S1 to S4, and their execution order as PC1, PC2, PC3, PC4 and PC5. Here, the imaging type S1 (hatched portion in the FIG. 11) of the new protocol PC corresponds to the merged element, and means the scanogram imaging associated with the first merged imaging area FS1. The imaging type S2 (hatched portion in the FIG. 11) of the new protocol PC corresponds to the merged element, and means the non-helical imaging associated with the first merged imaging area FS2.

The left part of FIG. 11 shows the imaging areas AS1 and BS1 of the original elements P41 and P51 corresponding to the scanogram imaging S1 in the two original protocols P4 and P5 to be used. An area including the imaging areas AS1 and BS1 is set as the first merged imaging area FS1. That is, the original elements P41 and P51 are merged in the imaging area of the scanogram imaging S1.

The middle part of FIG. 11 shows the imaging areas AS2 and BS2 of the original elements P42 and P52 corresponding to the non-helical imaging S2 in the two original protocols P4 and P5 to be used. An area including the imaging areas AS2 and BS2 is set as the first merged imaging area FS2. That is, the original elements P42 and P52 are merged in the imaging area of the non-helical imaging S2.

Returning to the explanation of FIG. 10, the protocol generating function 92 sets an imaging condition in the first merged imaging area set in step ST52 (step ST53A), and proceeds to step ST6 shown in FIG. 3. In step ST53A, the protocol generating function 92 may merge the imaging conditions. For example, when the imaging conditions of the imaging areas AS2 and BS2 of the non-helical imaging S2 shown in FIG. 11 are four times of imaging of 40 [mm] each, the protocol generating function 92 merges the imaging condition of the first merged imaging area FS2 into one time of imaging 160 [mm] in the new protocol.

According to the first modified example of the X-ray CT apparatus 10, it is possible to freely generate the new protocol, corresponding to small X-ray exposure to the patient O, and provide the operator with the new protocol, since the same imaging type is specified based on the original protocols, and the imaging areas of the original elements corresponding to the same imaging type are merged.

Second Modified Example

An execution order, in the case where a chest slice protocol including the non-contrast tomographic imaging (non-helical imaging or helical imaging) as the imaging type and a chest slice protocol including the contrast tomographic imaging as the imaging type are set to be used, will be described below. In this case, in step ST6 shown in FIG. 3, the protocol generating function 92 generates a new protocol by executing the execution order so that the non-contrast tomographic imaging is prior to the contrast tomographic imaging.

When the original protocols including the contrast tomographic imaging is set to be used respectively, the protocol generating function 92 organizes, in steps ST5 and ST6 shown in FIG. 3, the execution order so that the amount of the contrast agent becomes the minimum, thereby generating the new protocol. For example, when the original protocol to be used is an abdominal contrast protocol and a lower limb contrast protocol, the non-contrast imaging type and the contrast imaging type of the abdominal contrast protocol are performed in order, and the non-contrast imaging type and the contrast imaging type of the lower limb contrast imaging protocol are performed in order.

In this case, the protocol generating function 92 merges the imaging areas of the abdomen and the lower limb, and furthermore, the non-contrast imaging type related to the merged imaging area, the contrast imaging type related to the abdomen, the contrast imaging type related to the lower limb in order, thereby generating the new protocol. Utilizing the contrast agent for abdominal contrast as a contrast agent for the lower limb, it is able to reduce the contrast agent volume as a whole of the two abdominal contrast protocol and lower limb contrast protocol.

FIG. 12 is a diagram showing an example of a display screen of the new protocol.

The upper right part of FIG. 12 shows two original protocols P6 and P7 to be used. The lower right part of FIG. 12 shows the new protocol PC when the first merged imaging area FS1 is set. The new protocol PC includes six imaging elements corresponding to the four imaging types and an execution order of the five imaging elements. That is, the new protocol PC includes six imaging elements PC1 to PC6 corresponding to four imaging types S1 to S4, and their execution order as PC1, PC2, PC3, PC4 (contrast), PC5 (contrast) and PC6 (contrast). Here, the imaging type S1 (hatched portion in the FIG. 12) of the new protocol PC corresponds to the merged element, and means the scanogram imaging associated with the first merged imaging area FS1.

The left part of FIG. 12 shows the imaging areas AS1 and BS1 of the original elements P61 and P71 corresponding to the scanogram imaging S1 in the two original protocols P6 and P7 to be used. An area including the imaging areas AS1 and BS1 is set as the first merged imaging area FS1. That is, the original elements P61 and P71 are merged in the imaging area of the scanogram imaging S1.

According to the second modified example of the X-ray CT apparatus 10, it is possible to freely generate the new protocol, corresponding to small X-ray exposure to the patient O, and provide the operator with the new protocol, since the relevant imaging types are specified based on the original protocols, and the execution order of the original elements corresponding to the relevant imaging types are organized.

Third Modified Example

In the display screen of the new protocol shown in FIG. 8, it is also possible to display information changed before and after generation of the new protocol and an effect by optimization of the original protocols. For example, the information changed before and after generation of the new protocol means the amount of radiation exposure, examination time, amount of contrast agent used, total amount of mAs (product of tube current [mA] and time (sec.)), reconstruction time. The effect by the optimization is the difference of the information changed before and after the generation of the new protocol.

According to the third modified example of the X-ray CT apparatus 10, in addition to the above-mentioned effects, it is possible to present the effect by the optimization of the original protocols to the operator.

Fourth Modified Example

The protocol generating function 92, shown in FIG. 2, displays the original protocol and the new protocol on the display screen on the time axis basis, so that the operator can compare the both. The operator operates the input interface 82, referring to the new protocol on the display screen, therefore the protocol generating function 92 can edit time interval between the original elements included in the original protocol. If inconsistency occurs in the time interval, the protocol generating function 92 presents to that effect to the operator. The protocol generating function 92 can switchably display a display screen showing a time interval before editing and a display screen showing a time interval after editing.

Each of FIGS. 13 and 14 is a diagram showing an example of a time interval edit screen.

FIG. 13 shows three original protocols P1 to P3 to be used and a new protocol PC based thereon. Each of the three original protocols P1 to P3 includes original elements and their execution order, and also includes a time interval between specific original elements.

Here, when "original time" is selected on the display screen shown in FIG. 13, the time intervals related to the three original protocols P1 to P3 to be used and of the new protocol PC are displayed as the time intervals before editing. On the other hand, when "optimized time" is selected on the display screen, the time intervals of the three original protocols P1 to P3 to be used and of the new protocol PC are displayed as time intervals after editing.

FIG. 14 shows two original protocols P1 and P2 to be used and a new protocol PC based thereon. Each of the two original protocols P1 and P2 includes original elements and their execution order, and also includes a time interval between specific original elements.

Here, when "original time" is selected on the display screen shown in FIG. 14, the time intervals related to the two original protocols P1 and P2 to be used and of the new protocol PC are displayed as time intervals before editing. On the other hand, when "optimized time" is selected on the display screen, the time intervals of the two original protocols P1 and P2 to be used and of the new protocol PC are displayed as the time intervals after editing.

According to the fourth modified example of the X-ray CT apparatus 10, the time intervals between the original elements are visualized, and the operator can easily edit the time intervals.

2. Imaging Management Apparatus

FIG. 15 is a block diagram showing an exemplary configuration and functions of an imaging management apparatus according to an embodiment.

FIG. 15 shows an imaging management apparatus 110 and an X-ray CT apparatus C according to the embodiment. The imaging management apparatus 110 includes processing circuitry 181, a memory 182, an input interface 183, a display 184 and a network interface 185.

Here, the processing circuitry 181, the memory 182, the input interface 183 and the display 184 have the same configurations as the processing circuitry 81, the memory 82, the input interface 83 and the display 84 shown in FIG. 1, respectively, explanation of their configurations is omitted.

The network interface 185 implements various information communication protocols according to the form of the network. In accordance with these various protocols, the network interface 185 connects the imaging management apparatus 110 to the other device such as the external X-ray CT apparatus C. For this connection, electrical connection or the like via an electronic network can be applied. Here, the electronic network means the whole information communication network using the telecommunication technology. The electronic network includes a local area network (LAN) of a wireless/wired hospital backbone, an internet network, a telephone communication network, an optical fiber communication network, a cable communication network, a satellite communication network, and the like.

When the processing circuitry 181 executes the program, as shown in FIG. 15, the imaging management apparatus 110 achieves a setting function (setting unit) 191, a protocol generating function (protocol generating unit) 192, a providing function (providing unit) 193, and a transmitting function (transmitting unit) 194. All or part of the functions 191 to 194 may be achieved by a circuit such as the ASIC included in the imaging management apparatus 110.

Here, the functions 191 to 193 have the same function as the functions 91 to 93 shown in FIG. 2, respectively, explanation of their functions is omitted.

The transmitting function 194 includes a function of transmitting the new protocol generated by the protocol generating function 192 to the X-ray CT apparatus C via the network interface 185. As a result, the X-ray CT apparatus C can perform an imaging in accordance with the new protocol.

According to the imaging management apparatus 110, it is possible to freely generate the new protocol, corresponding to small X-ray exposure to the patient O in the X-ray CT apparatus C, and provide the operator with the new protocol, since the same imaging type is specified based on the original protocols, and the imaging areas of the original elements corresponding to the same imaging type are merged. Further, according to the imaging management apparatus 110, it is possible to reduce the examination time in the X-ray CT apparatus C, since the imaging conditions of the original elements corresponding to the same imaging type are optimized.

According to at least one embodiment described above, it is possible to generate the appropriate new protocol based on the original protocol.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus executing an imaging according to an imaging protocol including information of a body part to be imaged and including multiple imaging protocol elements corresponding to imaging types to be executed by the X-ray CT apparatus, the X-ray CT apparatus comprising:
an X-ray source configured to radiate an X-ray;
an X-ray detector configured to detect the X-ray, wherein the imaging is executed by the X-ray source and the X-ray detector; and
processing circuitry configured to:
set first and second imaging protocols to perform the imaging, wherein (1) the first imaging protocol includes n imaging protocol elements including a first imaging protocol element, which are the multiple imaging protocol elements and (2) the second imaging protocol includes m imaging protocol elements including a second imaging protocol element, which are the multiple imaging protocol elements;
generate, in a case where the first and second imaging protocol elements are of a same imaging type, a third imaging protocol consisting of n+m−1 imaging protocol elements including (1) a third imaging protocol element generated by merging the first and second imaging protocol elements, (2) n−1 imaging protocol elements of the n protocol elements from the first imaging protocol other than the first protocol element, and (3) m−1 imaging protocol elements of the m protocol elements from the second imaging protocol other than the second protocol element; and
generate an image by executing the imaging based on the third imaging protocol including the n+m−1 imaging protocol elements instead of executing the first and second imaging protocols separately.

2. The X-ray CT apparatus according to claim 1, wherein the same imaging type of the first and second imaging protocol elements is a scanogram imaging.

3. The X-ray CT apparatus according to claim 2, wherein the processing circuitry is configured to merge, from the first and second imaging protocol elements, overlapping parts of imaging areas to generate the third imaging protocol element.

4. The X-ray CT apparatus according to claim 1, wherein the same imaging type of the first and second imaging protocol elements is a tomographic imaging.

5. The X-ray CT apparatus according to claim 4, wherein the processing circuitry is configured to merge, from the first and second imaging protocol elements, overlapping parts of imaging areas to generate the third imaging protocol element.

6. The X-ray CT apparatus according to claim 5, wherein the processing circuitry is configured to set, when merging the first and second imaging protocol elements, an imaging condition based on the body part.

7. The X-ray CT apparatus according to claim 1, wherein the processing circuitry is configured to set an imaging condition of the third imaging protocol element based on imaging conditions of the first and second imaging protocol elements.

8. The X-ray CT apparatus according to claim 1, wherein the processing circuitry further configured to control the X-ray source and the X-ray detector to execute an imaging corresponding to the third imaging protocol.

9. The X-ray CT apparatus according to claim 8, wherein the processing circuitry is configured to display the image on a display based on the first and second imaging protocol elements or based on the third imaging protocol element.

10. The X-ray CT apparatus according to claim 1, wherein the imaging type of the first and second imaging protocol elements are different than one of the other n+m−1 imaging protocol elements.

11. The X-ray CT apparatus according to claim 10, wherein the processing circuitry is configured to generate the third imaging protocol by organizing an execution order of the n+m−1 imaging protocol elements included in the third imaging protocol.

12. The X-ray CT apparatus according to claim 11, wherein the processing circuitry is configured to perform, when the n+m−1 imaging protocol elements included in the third imaging protocol include a non-contrast imaging protocol element corresponding to the imaging type including non-contrast and a contrast imaging protocol element corresponding to the imaging type including contrast, the organization so that the non-contrast imaging protocol element precedes the contrast imaging protocol element.

13. The X-ray CT apparatus according to claim 11, wherein the processing circuitry is configured to perform, when the n+m−1 imaging protocol elements included in the third imaging protocol include multiple imaging protocol elements corresponding to the imaging type including contrast, the organization so as to minimize the amount of a contrast agent.

14. An X-ray CT apparatus executing an imaging according to an imaging protocol including information of a body part to be imaged and including multiple imaging protocol elements corresponding to imaging types to be executed by the X-ray CT apparatus, the X-ray CT apparatus comprising:
an X-ray source configured to radiate an X-ray;
an X-ray detector configured to detect the X-ray, wherein the imaging is executed by the X-ray source and the X-ray detector; and
processing circuitry configured to:
set first and second imaging protocols to perform the imaging;
generate a third imaging protocol organized such that a non-contrast imaging protocol element corresponding to the imaging type of non-contrast precedes a contrast imaging protocol element corresponding to the imaging type of contrast, wherein the non-contrast imaging protocol element is included in at least one of the set first and second imaging protocols, and the contrast imaging protocol element is included in at least one of the set first and second imaging protocols; and
execute the imaging based on the generated third imaging protocol.

15. The X-ray CT apparatus according to claim 14, wherein the processing circuitry configured to generate the third imaging protocol is configured to organize, when the multiple imaging protocol elements included in the third imaging protocol include multiple imaging protocol elements corresponding to the imaging type including contrast, the third imaging protocol so as to minimize an amount of a contrast agent.

16. An imaging management apparatus generating data related to an imaging protocol including information of a body part to be imaged and including multiple imaging protocol elements corresponding to imaging types to be executed by an X-ray CT apparatus and transmitting the data related to the imaging protocol to the X-ray CT apparatus, the imaging management apparatus comprising
processing circuitry configured to:
set first and second imaging protocols to perform the imaging, wherein (1) the first imaging protocol includes n imaging protocol elements including a first imaging protocol element, which are the multiple imaging protocol elements and (2) the second imaging protocol includes m imaging protocol elements including a second imaging protocol element, which are the multiple imaging protocol elements;
generate, in a case where the first and second imaging protocol elements are of a same imaging type, a third imaging protocol consisting of n+m−1 imaging protocol elements including (1) a third protocol element generated by merging the first and second imaging protocol elements, (2) n−1 imaging protocol elements of the n protocol elements from the first imaging protocol other than the first protocol element, and (3) m−1 imaging protocol elements of the m protocol elements from the second imaging protocol other than the second protocol element; and
transmit data of the third imaging protocol including the n+m−1 imaging protocol elements to the X-ray CT apparatus instead of transmitting the first and second imaging protocols separately.

17. An imaging management apparatus generating data related to an imaging protocol including information of a body part to be imaged and including multiple imaging protocol elements corresponding to imaging types to be executed by an X-ray CT apparatus and transmitting the data related to the imaging protocol to the X-ray CT apparatus, the imaging management apparatus comprising
processing circuitry configured to:
set first and second imaging protocols to perform the imaging;
generate a third imaging protocol organized such that a non-contrast imaging protocol element corresponding to the imaging type of non-contrast precedes a contrast imaging protocol element corresponding to the imaging type of contrast, wherein the non-contrast imaging protocol element is included in at least one of the set first and second imaging protocols, and the contrast imaging protocol element is included in at least one of the set first and second imaging protocols; and
transmit data of the generated third imaging protocol to the X-ray CT apparatus.

18. The X-ray CT apparatus according to claim 1, wherein the processing circuitry is configured to:
generate, in a case where each of the first and second imaging protocols includes imaging protocol elements corresponding to a scanogram imaging and a CT scan, the third imaging protocol element to indicate a scanogram imaging generated by merging scanogram imaging information corresponding to the first and second imaging protocol elements.

19. An X-ray CT apparatus executing an imaging according to an imaging protocol including information of a body part to be imaged and including multiple imaging protocol elements corresponding to imaging types to be executed by the X-ray CT apparatus, the X-ray CT apparatus comprising:
an X-ray source configured to radiate an X-ray;
an X-ray detector configured to detect the X-ray, wherein the imaging is executed by the X-ray source and the X-ray detector;
processing circuitry configured to:
set a first and a second imaging protocols to perform imaging; and
execute, in a case where the first imaging protocol includes, as imaging protocol elements, a first scanogram imaging and a first CT scan, and where the second imaging protocol includes, as imaging protocol elements, a second scanogram imaging and a second CT scan, a scanogram imaging corresponding to the first and second scanogram imaging, before a CT scan corresponding to the first and second CT scans.

* * * * *